United States Patent
Biederman et al.

(10) Patent No.: US 11,426,101 B2
(45) Date of Patent: Aug. 30, 2022

(54) SYSTEMS AND METHODS FOR SENSORS WITH MULTIMODE WIRELESS COMMUNICATIONS AND FOR ENABLING NFC COMMUNICATIONS WITH A WEARABLE BIOSENSOR

(71) Applicant: Verily Life Sciences LLC, South San Francisco, CA (US)

(72) Inventors: William Biederman, San Francisco, CA (US); Anil Kumar Ram Rakhyani, Union City, CA (US); Louis Jung, Foster City, CA (US); Stephen O'Driscoll, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/843,392

(22) Filed: Apr. 8, 2020

(65) Prior Publication Data
US 2020/0281467 A1 Sep. 10, 2020

Related U.S. Application Data

(63) Continuation-in-part of application No. 16/030,383, filed on Jul. 9, 2018, now abandoned, and a
(Continued)

(51) Int. Cl.
*A61B 5/145* (2006.01)
*A61B 5/00* (2006.01)
(Continued)

(52) U.S. Cl.
CPC .......... *A61B 5/14532* (2013.01); *A61B 5/002* (2013.01); *H01Q 1/36* (2013.01);
(Continued)

(58) Field of Classification Search
CPC ..... A61B 5/00–5/0031; A61B 5/14532; A61B 5/002; H04W 4/80; H04W 12/06; H04W 76/10; H01Q 1/36; H01Q 7/00
See application file for complete search history.

(56) References Cited

U.S. PATENT DOCUMENTS

| 7,031,945 B1 | 4/2006 | Donner |
| 8,798,541 B1 | 8/2014 | Scott |
(Continued)

FOREIGN PATENT DOCUMENTS

| CA | 2553507 | 11/2009 |
| CN | 101193671 | 6/2008 |
(Continued)

OTHER PUBLICATIONS

U.S. Appl. No. 15/218,587, "Advisory Action", dated Oct. 5, 2017, 3 pages.
(Continued)

*Primary Examiner* — Gennadiy Tsvey
(74) *Attorney, Agent, or Firm* — Kilpatrick Townsend & Stockton LLP

(57) ABSTRACT

One example system includes a biosensor applicator having a housing defining a cavity configured to receive and physically couple to a biosensor device, and to apply the biosensor device to a wearer; an applicator coil antenna oriented around a first axis; and a biosensor device including a biosensor coil antenna; a first wireless transceiver electrically coupled to the biosensor coil antenna; a Bluetooth antenna; and a second wireless transceiver coupled to the Bluetooth antenna; wherein the biosensor device is physically coupled to the biosensor applicator and positioned at least partially within the cavity; and wherein the applicator coil antenna is configured to wirelessly receive electromagnetic ("EM") energy from a remote coil antenna and wire-
(Continued)

lessly provide at least a first portion of the received EM energy to the biosensor coil antenna.

14 Claims, 13 Drawing Sheets

Related U.S. Application Data continuation-in-part of application No. 16/528,798, filed on Aug. 1, 2019.

(60) Provisional application No. 62/714,799, filed on Aug. 6, 2018.

(51) Int. Cl.

| | |
|---|---|
| *H04W 4/80* | (2018.01) |
| *H04W 12/06* | (2021.01) |
| *H04W 76/10* | (2018.01) |
| *H01Q 1/36* | (2006.01) |
| *H01Q 7/00* | (2006.01) |
| *H04W 88/06* | (2009.01) |

(52) U.S. Cl.
CPC ............... *H01Q 7/00* (2013.01); *H04W 4/80* (2018.02); *H04W 12/06* (2013.01); *H04W 76/10* (2018.02); *A61B 2560/0223* (2013.01); *H04W 88/06* (2013.01)

(56) References Cited

U.S. PATENT DOCUMENTS

| | | | |
|---|---|---|---|
| 8,947,041 B2 | 2/2015 | Cook et al. | |
| 9,110,897 B2 | 8/2015 | Park et al. | |
| 9,246,555 B2 | 1/2016 | Griffin et al. | |
| 9,901,293 B2 | 2/2018 | Dehennis et al. | |
| 9,949,642 B2* | 4/2018 | Love ..................... | A61B 5/002 |
| 9,967,001 B2 | 5/2018 | Biederman | |
| 2003/0012566 A1 | 1/2003 | Kindaichi | |
| 2003/0050009 A1 | 3/2003 | Kurisko et al. | |
| 2006/0173260 A1 | 8/2006 | Gaoni et al. | |
| 2007/0008139 A1 | 1/2007 | Saarisalo et al. | |
| 2008/0116847 A1 | 5/2008 | Loke et al. | |
| 2010/0045425 A1 | 2/2010 | Chivallier | |
| 2010/0148723 A1 | 6/2010 | Cook et al. | |
| 2010/0292556 A1 | 11/2010 | Golden | |
| 2011/0022411 A1 | 1/2011 | Hjelm et al. | |
| 2011/0046548 A1 | 2/2011 | Sakata et al. | |
| 2011/0221590 A1 | 9/2011 | Baker et al. | |
| 2012/0003933 A1 | 1/2012 | Baker et al. | |
| 2012/0028575 A1 | 2/2012 | Chen et al. | |
| 2012/0157801 A1* | 6/2012 | Hoss .................. | A61B 5/14503 600/309 |
| 2013/0029596 A1 | 1/2013 | Preston et al. | |
| 2013/0069753 A1 | 3/2013 | Kurs et al. | |
| 2013/0217979 A1 | 8/2013 | Blackadar et al. | |
| 2013/0274629 A1 | 10/2013 | Duesterhoft et al. | |
| 2014/0138432 A1 | 5/2014 | Park et al. | |
| 2014/0184422 A1 | 7/2014 | Mensinger et al. | |
| 2014/0273821 A1 | 9/2014 | Miller et al. | |
| 2014/0313052 A1 | 10/2014 | Yarger et al. | |
| 2015/0018643 A1 | 1/2015 | Cole et al. | |
| 2015/0054621 A1 | 2/2015 | Lin et al. | |
| 2015/0075770 A1 | 3/2015 | Fripp et al. | |
| 2015/0182153 A1* | 7/2015 | Feldman ............... | A61B 5/7235 600/309 |
| 2015/0343144 A1 | 12/2015 | Altschul et al. | |
| 2016/0015267 A1 | 1/2016 | Bernstein et al. | |
| 2016/0183854 A1 | 6/2016 | Lee | |
| 2016/0242685 A1 | 8/2016 | DeHennis et al. | |
| 2016/0310663 A1 | 10/2016 | Dantsker | |
| 2016/0331232 A1 | 11/2016 | Love et al. | |
| 2016/0331283 A1 | 11/2016 | Rao et al. | |
| 2017/0040818 A1 | 2/2017 | Kong et al. | |
| 2017/0047636 A1 | 2/2017 | Lee et al. | |
| 2017/0079587 A1 | 3/2017 | Fougere et al. | |
| 2017/0173262 A1 | 6/2017 | Veltz | |
| 2017/0185284 A1 | 6/2017 | Bhavaraju et al. | |
| 2017/0337461 A1 | 11/2017 | Jesme et al. | |
| 2018/0026678 A1 | 1/2018 | Biederman | |
| 2018/0182491 A1 | 6/2018 | Belliveau et al. | |
| 2018/0192514 A1 | 7/2018 | Seo | |
| 2018/0199813 A1 | 7/2018 | Love et al. | |
| 2018/0234133 A1 | 8/2018 | Biederman | |
| 2019/0374138 A1* | 12/2019 | Frey ....................... | A61B 5/145 |
| 2020/0044695 A1 | 2/2020 | Biederman et al. | |

FOREIGN PATENT DOCUMENTS

| | | |
|---|---|---|
| CN | 102144239 | 8/2011 |
| CN | 204576485 | 8/2015 |
| CN | 105686807 | 6/2016 |
| WO | 2013063634 | 5/2013 |
| WO | 2016081244 | 5/2016 |
| WO | 2016205373 | 12/2016 |
| WO | 2018022235 | 2/2018 |

OTHER PUBLICATIONS

U.S. Appl. No. 15/218,587, "Final Office Action", dated Jul. 24, 2017, 16 pages.

U.S. Appl. No. 15/218,587, "Non-Final Office Action", dated Jan. 12, 2017, 13 pages.

U.S. Appl. No. 15/218,587, "Notice of Allowance", dated Jan. 10, 2018, 8 pages.

U.S. Appl. No. 15/945,286, "Advisory Action", dated Feb. 7, 2019, 3 pages.

U.S. Appl. No. 15/945,286, "Final Office Action", dated Nov. 2, 2018, 19 pages.

U.S. Appl. No. 15/945,286, "Non Final Office Action", dated Jun. 4, 2018, 17 Pages.

U.S. Appl. No. 16/030,383, "Advisory Action", dated Feb. 19, 2020, 3 pages.

U.S. Appl. No. 16/030,383, "Advisory Action", dated Apr. 12, 2019, 5 pages.

U.S. Appl. No. 16/030,383, "Final Office Action", dated Nov. 19, 2019, 25 pages.

U.S. Appl. No. 16/030,383, "Final Office Action", dated Feb. 8, 2019, 26 pages.

U.S. Appl. No. 16/030,383, "Non-Final Office Action", dated Oct. 9, 2018, 22 pages.

U.S. Appl. No. 16/030,383, "Non-Final Office Action", dated Jul. 12, 2019, 24 pages.

Chinese Application No. 201780046360.7, "Office Action", dated Nov. 11, 2019, 9 pages.

Jara et al., "Communication Protocol for Enabling Continuous Monitoring of Elderly People through Near Field Communications", Interacting with Computers, May 15, 2013, 2 pages.

International Application No. PCT/US2017/039380, "International Preliminary Report on Patentability", dated Feb. 7, 2019, 8 pages.

International Application No. PCT/US2017/039380, "International Search Report and Written Opinion", dated Sep. 7, 2017, 11 pages.

U.S. Appl. No. 16/528,798, Notice of Allowance, dated Feb. 16, 2021, 8 pages.

Taiwan Application No. 106124488, Office Action, dated Feb. 23, 2021, 8 pages.

U.S. Appl. No. 16/528,798, Advisory Action, dated Jan. 13, 2021, 3 pages.

EP Application No. 17735752.2, Office Action, dated Nov. 24, 2020, 6 pages.

U.S. Appl. No. 16/528,798, Final Office Action, dated Oct. 6, 2020, 13 pages.

"NFC Antenna : Add-on for your NFC Patch", Available Online at: <https://flomio.com/shop/readers/nfc-antenna/>, Accessed from Internet on Oct. 14, 2019, 5 pages.

"NFC Patch Kit: Extend your NFC reach", Available Online at: <https://flomio.com/shop/nfc-readers/nfc-patch-kit/>, Accessed from Internet on Oct. 14, 2019, 4 pages.

(56) References Cited

OTHER PUBLICATIONS

U.S. Appl. No. 16/528,798, Non-Final Office Action, dated Jun. 26, 2020, 12 pages.
Chinese Application No. 201780046360.7, Notice of Decision to Grant, dated Jul. 3, 2020, 2 pages.
International Application No. PCT/US2019/044789, International Search Report and Written Opinion, dated Nov. 7, 2019, 12 pages.
European Application No. 19847883.6, Extended European Search Report, dated Apr. 7, 2022, 8 pages.

* cited by examiner

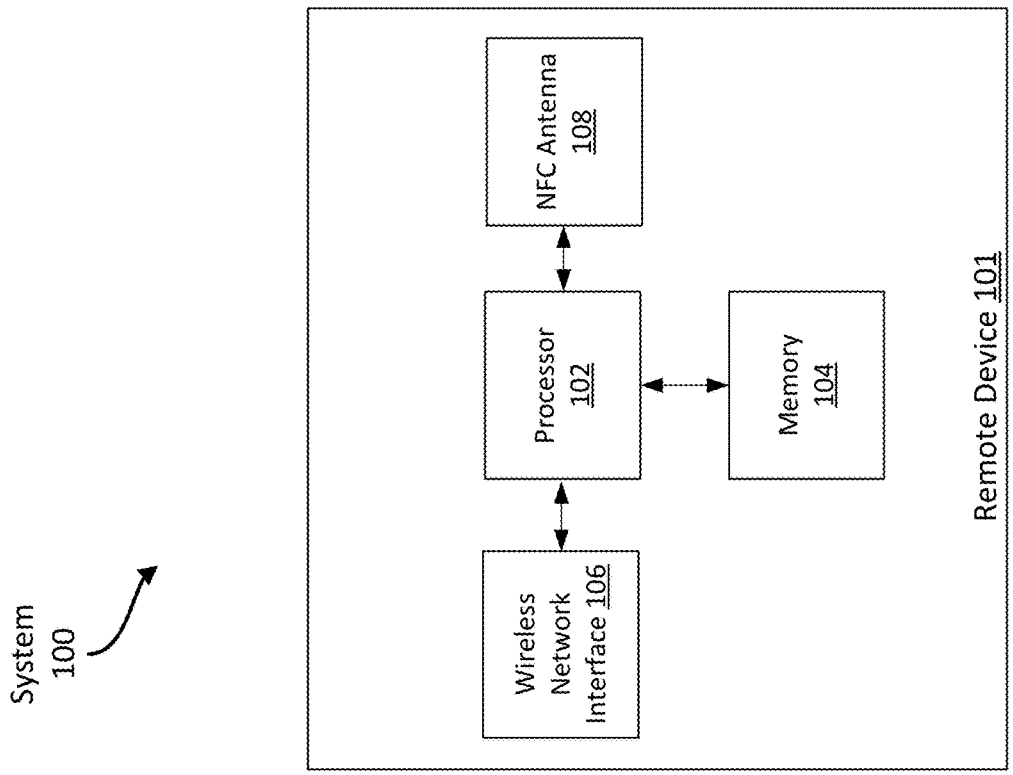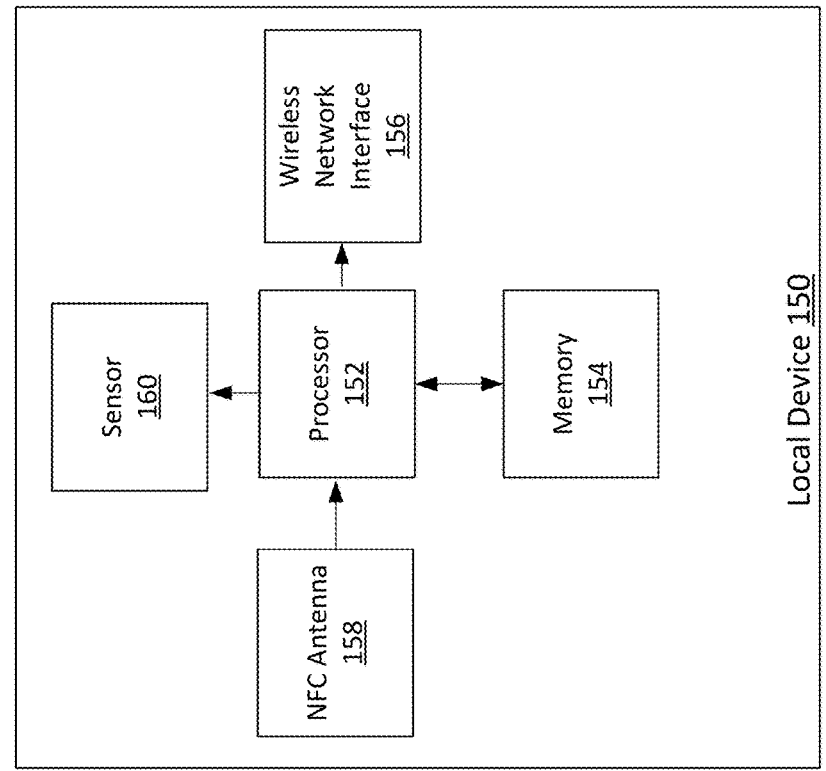
FIG. 1

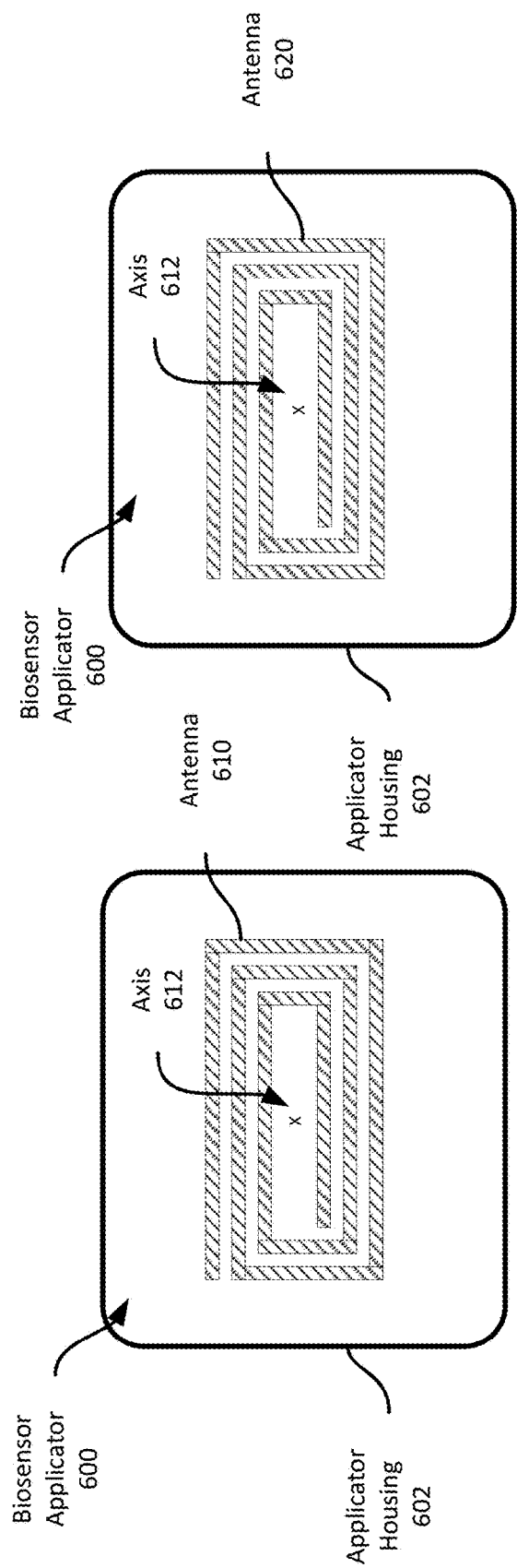
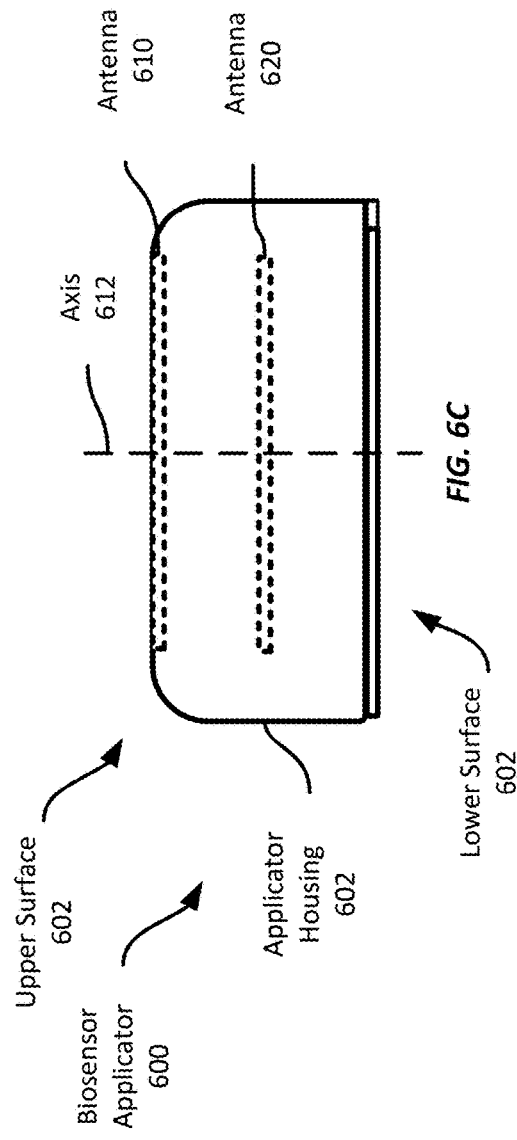
FIG. 6A
FIG. 6B
FIG. 6C

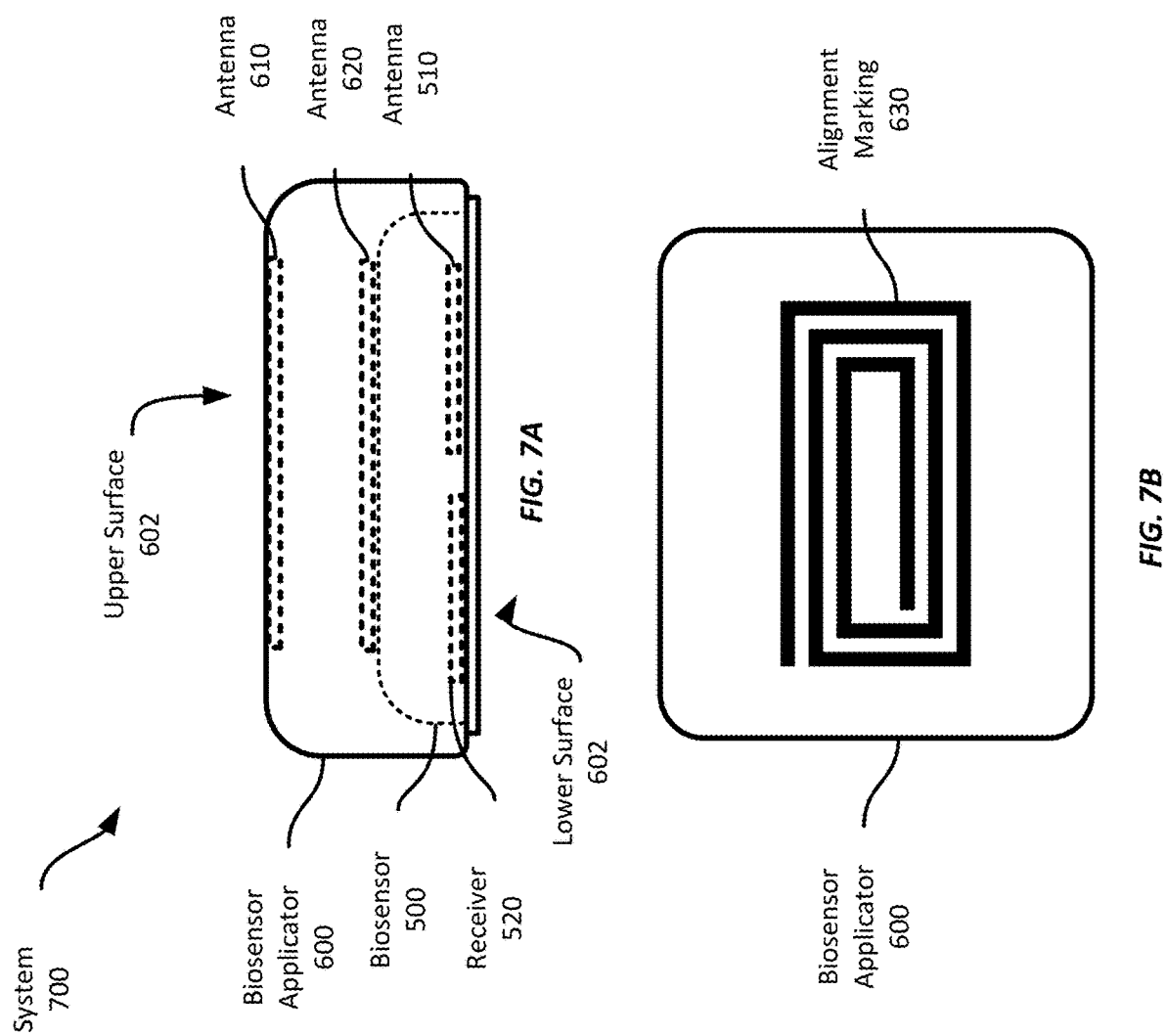

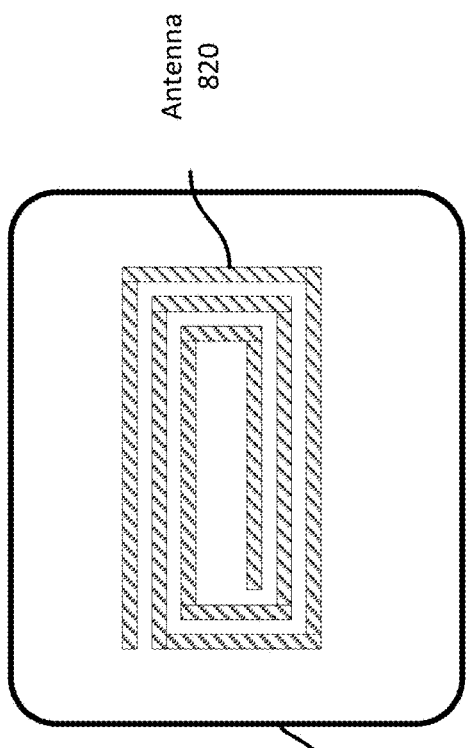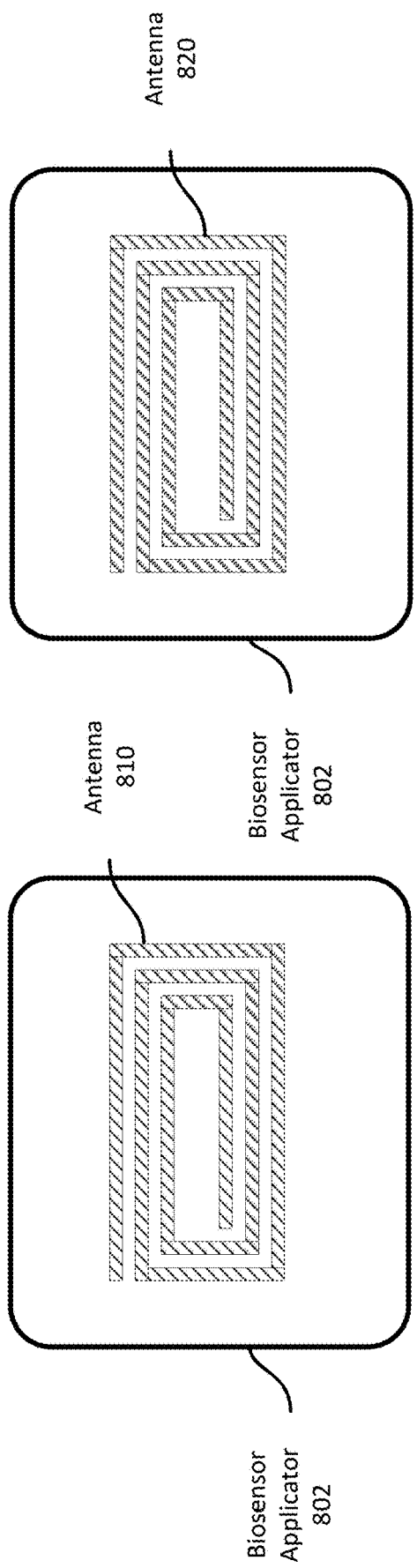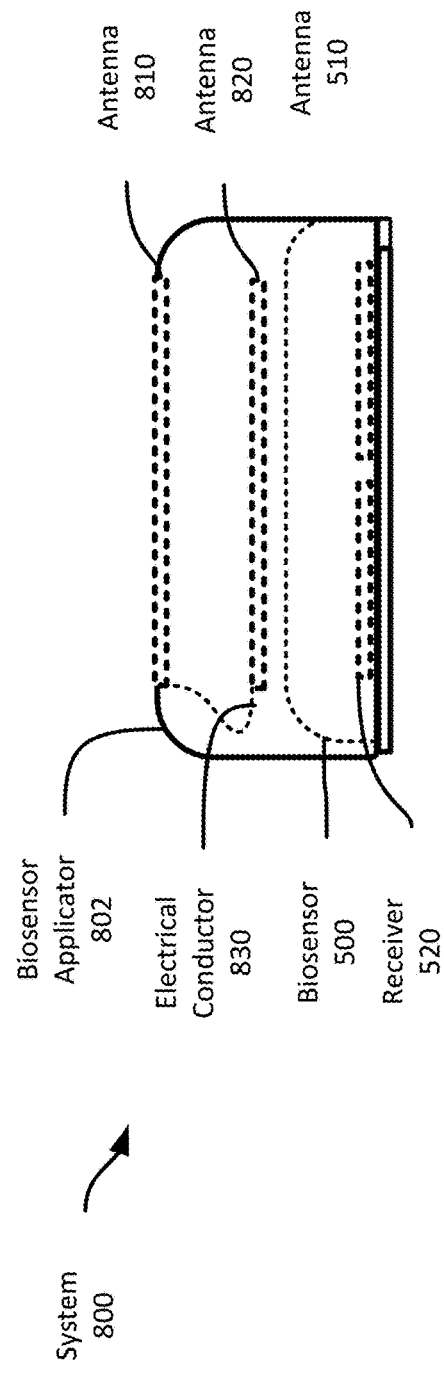

SYSTEMS AND METHODS FOR SENSORS WITH MULTIMODE WIRELESS COMMUNICATIONS AND FOR ENABLING NFC COMMUNICATIONS WITH A WEARABLE BIOSENSOR

CROSS REFERENCE TO RELATED APPLICATION

This application is a continuation-in-part of co-pending U.S. application Ser. No. 16/030,383 filed Jul. 9, 2018, titled "Systems And Methods For Enabling NFC Communications With A Wearable Biosensor" and a continuation-in-part of co-pending U.S. application Ser. No. 16/528,798 filed Aug. 1, 2019, which claims the benefit of U.S. Application No. 62/714,799, filed Aug. 6, 2018, titled "Systems And Methods For Enabling NFC Communications With A Wearable Biosensor," which each are incorporated herein by reference in their entireties.

BACKGROUND

Single use wearable sensors are becoming more popular. For many such sensors the period of time the sensor is worn by the user is a relatively small percentage of the lifetime of the sensor. For example, these sensors may comprise active components, e.g., a processor, memory, sensor, etc., which are powered by an onboard battery. However, one or more of these components may consume energy when the device is technically "off." For example, in some devices the processor must remain in a "low power" mode to detect whether the user has pressed the "on" button. However, storage and shipment prior to use may take many months. Thus, a significant portion of the total battery capacity may be consumed during storage prior to activation by the end user.

In addition, computing devices may communicate with other computing devices using wireless communications techniques, such as Bluetooth ("BT"), BT low-energy ("BLE"), WiFi, near-field communications ("NFC"), etc. Depending on the type of wireless communication technique employed, the computing devices may be located at great distances from each other, or may need to be brought into close proximity. In addition, different wireless communication techniques may require different levels of power consumption to enable effective wireless communication. Thus, different wireless communication techniques may be suited for different types of computing devices or use cases than others.

SUMMARY

In one embodiment, a system of the present disclosure may comprise: a continuous glucose monitor comprising: a Near Field Communication (NFC) antenna configured to receive NFC signals; a second antenna configured to receive Bluetooth Low Energy (BLE) wireless signals; a first sensor configured to measure blood glucose information; and a processor configured to: receive from the NFC antenna data signals from a remote device, the data signals comprising BLE authentication information; compare the BLE authentication information to device information associated with the continuous glucose monitor; enable a BLE network connection to the remote device based on the BLE authentication information; and transmit data associated with blood glucose information to the remote device using the BLE network connection.

In another embodiment, a method of the present disclosure may comprise: receiving data signals from a Near Field Communication (NFC) antenna configured to receive NFC signals from a remote device, the data signals comprising BLE authentication information; enabling a BLE network connection to the remote device based on the BLE authentication information; and transmitting data associated with blood glucose information to the remote device using the BLE network connection.

Another embodiment of the present disclosure may comprise a computer readable medium comprising program code configured, when executed by a processor, to cause the processor to: receive data signals from a Near Field Communication (NFC) antenna configured to receive NFC signals from a remote device, the data signals comprising BLE authentication information; enable a BLE network connection to the remote device based on the BLE authentication information; and transmit data associated with blood glucose information to the remote device using the BLE network connection.

Another example system includes a biosensor applicator comprising: a housing defining a cavity configured to receive and physically couple to a biosensor device, and to apply the biosensor device to a wearer; a first applicator coil antenna physically coupled to the housing and defined within a first plane; and a second applicator coil antenna physically coupled to the housing and defined within a second plane substantially parallel to and different from the first plane, the second applicator coil antenna positioned coaxially with respect to the first applicator coil antenna, wherein the first applicator coil antenna is configured to wirelessly receive electromagnetic ("EM") energy from a transmitter coil antenna of a remote device and provide at least a first portion of the received EM energy to the second coil antenna; and a biosensor device comprising: a biosensor coil antenna defined within a third plane substantially parallel to and different than the first and second planes; a wireless receiver electrically coupled to the biosensor coil antenna; wherein the biosensor device is physically coupled to the biosensor applicator and positioned within the cavity; wherein the biosensor coil antenna is positioned and oriented substantially coaxially with respect to the second applicator coil antenna, and wherein the second applicator coil antenna is configured to receive EM energy from the first applicator coil antenna and wirelessly transmit at least a second portion of the received EM energy to the biosensor coil antenna.

One example biosensor applicator includes a biosensor applicator housing configured to receive and physically couple to a biosensor device, the biosensor applicator configured to apply the biosensor device to a wearer; a first coil antenna physically coupled to the biosensor applicator housing; and a second coil antenna physically coupled to the biosensor applicator housing, the second coil antenna located distant from the first coil antenna and substantially co-axially aligned with the first coil antenna, and wherein the first coil antenna is configured to: wirelessly receive electromagnetic ("EM") energy from a transmitter coil antenna; and provide at least a portion of the received EM energy to the second coil antenna.

A further example biosensor applicator includes a biosensor applicator housing configured to receive and physically couple to a biosensor device, the biosensor applicator configured to apply the biosensor device to a wearer; a first coil antenna; wherein the first coil antenna is configured to: wirelessly receive electromagnetic ("EM") energy from a transmitter coil antenna, and provide at least a portion of the received EM energy to a biosensor coil antenna of a biosensor device.

One example method includes generating, using an electronic device, an alternating electromagnetic field ("EMF"), the electronic device comprising a wireless transmitter and a transmitter coil antenna, the wireless transmitter electrically coupled to the wireless transmitter; receiving, by a first coil antenna of a biosensor applicator, energy from the alternating EMF, wherein the biosensor applicator comprises: the first coil antenna; and a second coil antenna, the second coil antenna located distant from and substantially co-axially aligned with the first coil antenna; transmitting, by the first coil antenna, energy received from the alternating EMF to the second coil antenna; transmitting, by the second coil antenna, energy received from the first coil antenna to a biosensor coil antenna of a biosensor device, wherein the biosensor device comprises the biosensor coil antenna and a wireless receiver, the biosensor coil antenna electrically coupled to the wireless receiver.

A further example method includes generating, using an electronic device, an alternating electromagnetic field ("EMF"), the electronic device comprising a wireless transmitter and a transmitter coil antenna electrically coupled to the wireless transmitter; receiving, by a first coil antenna of a biosensor applicator, energy from the alternating EMF, the biosensor applicator comprising the first coil antenna; and transmitting, by the first coil antenna to a biosensor coil antenna, the energy received from the alternating EMF.

One example system for sensors with multimode wireless communications and for enabling NFC communications with a wearable biosensor includes a biosensor applicator includes a housing defining a cavity configured to receive and physically couple to a biosensor device, and to apply the biosensor device to a wearer; an applicator coil antenna oriented around a first axis; and a biosensor device comprising: a biosensor coil antenna; a first wireless transceiver electrically coupled to the biosensor coil antenna; a Bluetooth antenna; and a second wireless transceiver coupled to the Bluetooth antenna; wherein the biosensor device is physically coupled to the biosensor applicator and positioned at least partially within the cavity; and wherein the applicator coil antenna is configured to wirelessly receive electromagnetic ("EM") energy from a remote coil antenna and wirelessly provide at least a first portion of the received EM energy to the biosensor coil antenna.

An example biosensor device for sensors with multimode wireless communications and for enabling NFC communications with a wearable biosensor includes a biosensor applicator includes a biosensor coil antenna; a first wireless transceiver electrically coupled to the biosensor coil antenna; a Bluetooth antenna; a second wireless transceiver coupled to the Bluetooth antenna; and a processor configured to: receive, from the first wireless transceiver, data signals from a remote device, the data signals comprising Bluetooth authentication information; compare the Bluetooth authentication information to device information associated with the biosensor device; enable a Bluetooth network connection to the remote device based on the Bluetooth authentication information; determine a level of access of a plurality of levels of access to sensor data stored in a memory based on the data signals; and control access by the remote device to the sensor data stored in the memory based on the level of access.

An example method for sensors with multimode wireless communications and for enabling NFC communications with a wearable biosensor includes wirelessly receiving, by an applicator antenna coil, electromagnetic ("EM") energy from a remote coil antenna of a remote device, the EM energy comprising data signals; wirelessly providing at least a first portion of the received EM energy to a biosensor coil antenna of a biosensor device, the at least a first portion of the received EM energy comprising the data signals, the data signals comprising Bluetooth authentication information; wirelessly receiving by a processor of the biosensor device, the data signals from the biosensor coil antenna; compare the Bluetooth authentication information to device information associated with the biosensor device; and enable a Bluetooth network connection to the remote device based on the Bluetooth authentication information, and wherein the applicator coil antenna is a part of a biosensor applicator; the biosensor coil antenna is a part of a biosensor device, and the biosensor device is physically coupled to the biosensor applicator.

A further example method for sensors with multimode wireless communications and for enabling NFC communications with a wearable biosensor includes receiving, from a first wireless transceiver of a biosensor device, data signals from a remote device antenna coil via re-radiation by an applicator antenna coil, the data signals comprising Bluetooth authentication information; comparing the Bluetooth authentication information to device information associated with the biosensor device; enabling a Bluetooth network connection to the remote device based on the Bluetooth authentication information; determining a level of access of a plurality of levels of access to sensor data stored in a memory based on the data signals; and controlling access by the remote device to the sensor data stored in the memory based on the level of access.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

FIG. 1 shows an illustrative system for a sensor with multimode wireless communication according to one embodiment;

FIGS. 6A-6C show an example wearable biosensor applicator;

FIGS. 7A-7B show an example system for enabling NFC communications with a wearable biosensor;

FIGS. 8A-8C show an example wearable biosensor applicator and an example system for enabling NFC communications with a wearable biosensor;

DETAILED DESCRIPTION

Figure 2:
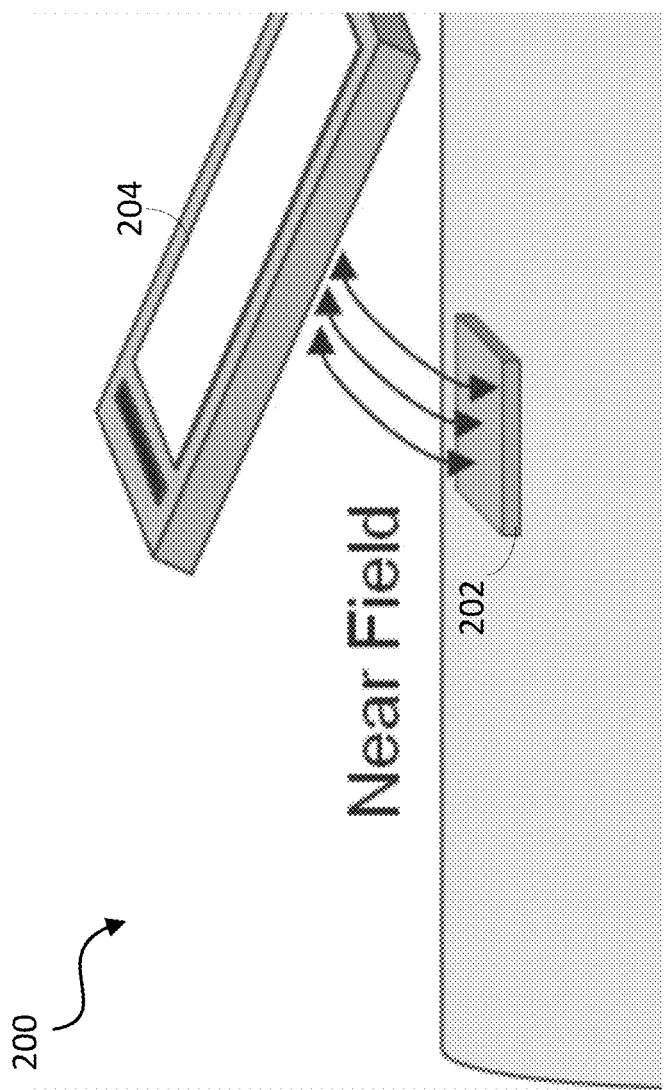
FIG. 2 shows an illustrative system for a sensor with multimode wireless communication according to one embodiment.

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of a Sensor with Multimode Wireless Communication

One illustrative embodiment of the present disclosure comprises a biometric sensor (e.g., a sensor to monitor brain activity, an Electrocardiogram (EKG), Electroencephalograph (EEG), Magnetoencephalograph (MEG), heart-rate monitor, blood pressure sensor, or analyte sensor, etc.) to monitor biometric information about a user. In some embodiments the biometric sensor may comprise a wearable sensor (the "wearable sensor"). In some embodiments, such a wearable sensor is configured to store monitored data and periodically transmit that data to a remote device.

In the illustrative embodiment, the wearable sensor may comprise a Near Field Communication (NFC) antenna configured to receive NFC signals from a remote device. These NFC signals may activate functionality within the wearable sensor. For example, in one embodiment, NFC signals may be used to generate energy. This energy may then be used to close a switch and thereby apply power from a power supply to components within the wearable sensor. Further, in some embodiments, the NFC signals may activate data transmission functionality in the wearable sensor. Thus, when the NFC antenna detects NFC signals, it may transmit a signal to a processor that activates a network interface, e.g., a Bluetooth or Bluetooth Low Energy (BLE) network interface that transmits data to, or receives data from, the remote device.

In the illustrative embodiment, NFC signals are received from a remote device positioned near (e.g., within 2-5 cm) of the wearable sensor. In the illustrative embodiment the remote device comprises a handheld mobile device, e.g., a smartphone. The smartphone also comprises an NFC antenna and functionality to transmit NFC signals via the NFC antenna. Further, in some embodiments, information may be encoded in the NFC signals transmitted by the remote device.

In some embodiments, the remote device may transmit control information to, or receive control information from, the wearable sensor. This control information may comprise, e.g., data associated with activating and pairing a Bluetooth or Bluetooth Low Energy (BLE) network interface on the wearable device with a similar network interface on the remote device. For example, in such an embodiment, when an NFC antenna on the wearable sensor detects an NFC signal it may activate a processor on the wearable device.

The processor then decodes data stored in the NFC signals and activates a Bluetooth or BLE network interface based on the signals. The processor may further decode Bluetooth key information, a network address, login information, authentication information, or passcode information from the NFC signals and use this information to pair the wearable sensor with the remote device via Bluetooth or BLE. This may simplify the process of coupling a network connection between the remote device and the local device because the user is not required to manually enter network information, which instead may be transmitted via NFC signals.

Further, this may enhance security of the process of authenticating the network because a remote device may not be able to pair with the local device without first receiving NFC data from the local device or transmitting NFC data to the local device. This enhances security because only devices that are close enough to the local device to receive NFC signals will be able to pair, providing security be proximity. Further, in some embodiments, authentication information may be changed each time a remote device pairs with the local device, thus ensuring that only the intended remote device is able to pair with the local device. These security features may be important in healthcare/biosensor applications in which security, both for privacy and to comply with government regulations, e.g., HIPAA (Health Insurance Portability and Accountability Act), are a concern to the wearer and/or the healthcare provider.

Such an illustrative embodiment may conserve energy, because a network interface of the embedded device can be inactive until a recipient device (e.g., the smartphone that output NFC signals) is available to receive transmitted data. Further, in some embodiments additional control information may be transmitted from the remote device to the wearable sensor once the devices are paired using the network connection as this connection may be faster than NFC. Thus, for example, once the devices are paired via a network connection (e.g., Bluetooth or BLE) control information may be sent to the wearable sensor. This control information may comprise, e.g., calibration information for one or more sensors of the wearable sensor, software or firmware updates, control information to cause the wearable sensor to transmit sensor data in real-time or to store sensor data for later transmission.

Further, in some embodiments, the remote device may comprise a device controlled by different types of users, e.g., the wearer of a local device, a healthcare provider, or a caretaker of the wearer. For example, the wearer of the remote device may be interested in tracking data in real time, whereas a healthcare provider may extract data that is collected over a longer period of time and stored. A healthcare provider may also calibrate or recalibrate sensor on the wearable device. Further, in some embodiments, the profile of the user of the remote device may control the level of access that the user is granted to the wearable device. In some embodiments, this level of access may be controlled based on data transmitted from the remote device to the local device via NFC, and thereby provide a further layer of security to user data collected on or stored in the local device.

In addition, wearable biosensors may be used for a variety of different reasons and may be used to sense many different physiological characteristics of a wearer. For example, referring to FIG. 4, a diabetic may wear a continuous glucose monitor ("CGM") 420 to monitor her glucose levels and determine whether she needs a dose of insulin or needs to consume some food. To apply the CGM 420, the wearer purchases a new CGM 420 and removes it from the package.

The CGM 420 is installed within a CGM applicator 430, which is a device that helps the user apply the CGM 420 to her body, such as by puncturing her skin to enable the CGM's sensor wire to be inserted beneath her skin. Before she applies the CGM 420, however, she first activates the CGM 420.

Figure 4:
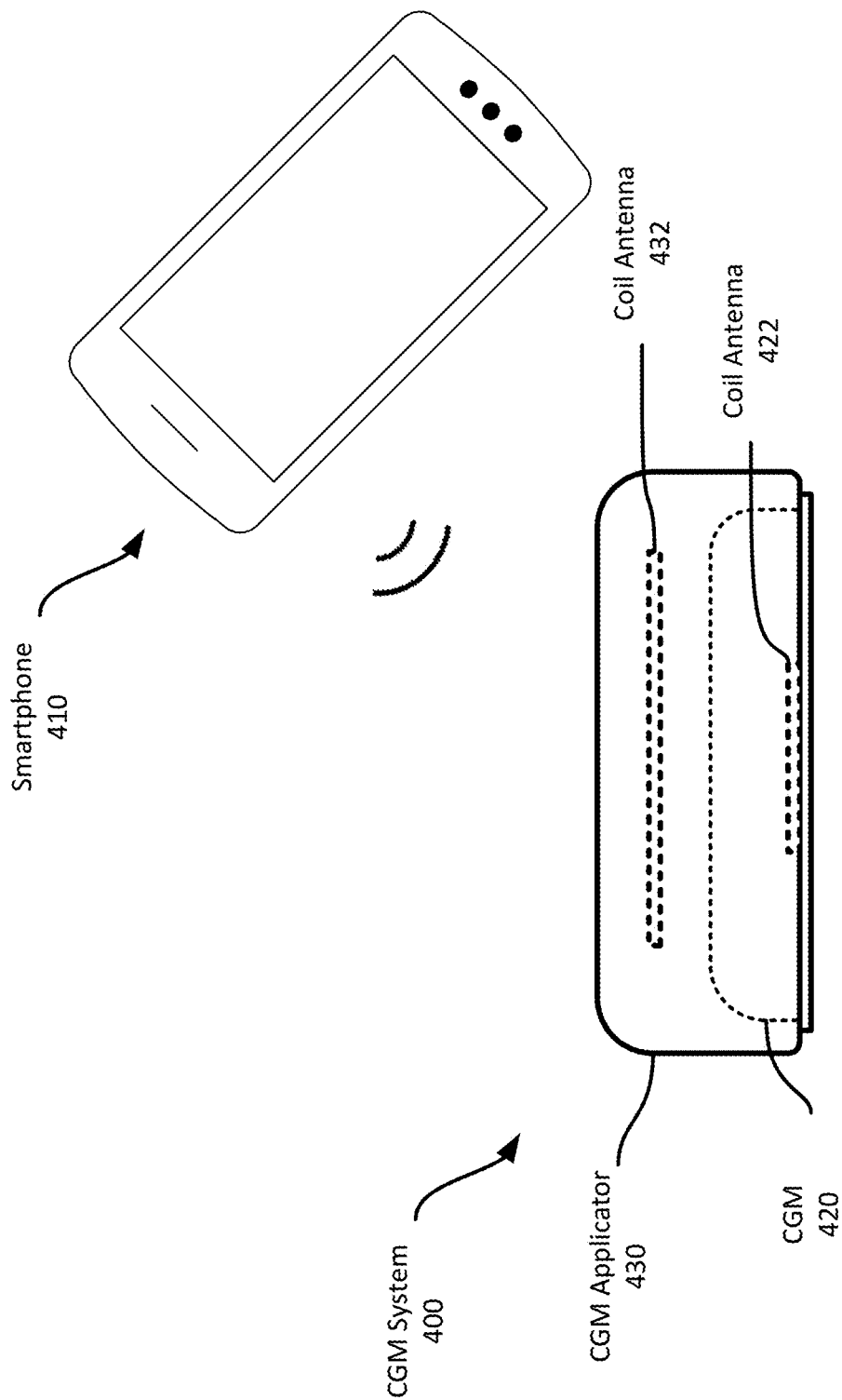
FIG. 4 shows an example system for enabling NFC communications with a wearable biosensor.

In this example, the CGM 420 is configured to use NFC communications to communicate with the wearer's smartphone 410 (or other computing device) as shown in FIG. 4. However, because the CGM 420 is installed within the CGM applicator 430, and NFC has a relatively short effective communications range, the CGM applicator 430 itself may prevent the NFC communication between the user's smartphone and the CGM 420, simply by being a physical barrier between the smartphone and the CGM 420 that prevents the two from being positioned closely enough to enable NFC communications.

To alleviate this potential problem, the CGM applicator 430 has an NFC coil antenna embedded within it. The CGM applicator's coil antenna 432 can receive NFC communications from the smartphone 410 and relay them to the CGM's NFC antenna 422. In this example, to help enable this relay functionality, the CGM applicator's coil antenna 432 is co-axially aligned with the CGM's coil antenna 422. When a varying electromagnetic field ("EMF") is applied to the CGM applicator's coil antenna 432, it energizes and is able to electromagnetically couple with the CGM's coil antenna 422, thereby transferring energy from the received EMF to the CGM's coil antenna 422 and NFC receiver.

Thus, to activate the CGM 420, the wearer launches an app on her smartphone 410 and selects an option to activate a new CGM. The app then activates the smartphone's NFC communication system and energizes its coil antenna to generate a varying EMF. Since NFC has an effective communications range on the order of a few centimeters to a few tens of centimeters, she brings her smartphone close to the new CGM system 400, which includes the CGM applicator 430 and the CGM 420. She then aligns her smartphone with a coil antenna within the CGM applicator 430, such as by visually locating the coil antenna 432 itself, or finding one or more alignment markings on the CGM applicator 430.

When she brings the smartphone 410 near the CGM applicator's coil antenna 432, i.e., she brings the smartphone 410 within the effective transmission range of the CGM applicator's coil antenna 432, the generated EMF electromagnetically couples the smartphone's coil antenna with the CGM applicator's coil antenna 432. The CGM applicator's coil antenna 432, after receiving the energy from the EMF, electromagnetically couples with the CGM's coil antenna 422 and transfers the energy to the CGM using the electromagnetic coupling.

In this example, the varying EMF field generated by the wearer's smartphone 410 includes an activation command that is propagated to the CGM 420 via the coil antennas as discussed above. After receiving the activation command, the CGM 420 activates and transmits a confirmation to the smartphone 410 using the same propagation technique, but in reverse from the CGM 420 back to the smartphone 410. Upon receiving the confirmation from the CGM 420, the app presents a notification to the wearer that the CGM 420 was successfully activated.

After receiving confirmation that the CGM 420 has been activated, the wearer then uses the CGM applicator 430 to apply the CGM 420 to her body and affix it to her skin. She then discards the CGM applicator 430, leaving the CGM 420 in place.

The CGM applicator 430 in this example enables NFC communications between the wearer's smartphone 410 (or other computing device) and the CGM's NFC receiver by providing an intermediate coil antenna to relay EMF energy to the CGM. The EMF energy may be used to send commands to the CGM or to power the CGM (or both). Thus, the CGM applicator enables NFC communications that might otherwise be prevented or degraded because the CGM applicator itself prevents the wearer's smartphone 410 from moving within effective communications range of the CGM's coil antenna 422, or otherwise interferes with communication between the two. And while the example above was in the context of a CGM and CGM applicator, any suitable biosensor device, including wearable biosensors, may be employed according to different examples. Further, and as will be discussed in more detail below, other intermediate coil configurations including multiple coils may be employed in some examples to extend the range of NFC communications between a smartphone (or other wireless computing device) and a receiving coil antenna. By extending the range of NFC communications, it can further ease the process of establishing wireless communications with the CGM 420, e.g., to establish a Bluetooth or BLE connection.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for a Sensor with Multimode Wireless Communication

FIG. 1 shows an illustrative system 100 for a sensor with multimode wireless communication. As shown in FIG. 1 the system comprises a remote device 101 and a local device 150. In the embodiment shown in FIG. 1, the remote device 101 may comprise a device that is not generally worn by the user of the local device 150. For example, in some embodiments, the remote device 101 may comprise, e.g., a mobile device (smartphone, tablet, laptop, or other handheld device) or a dedicated medical interface device, such as a heart monitor, blood pressure monitor, etc. The remote device 101 may comprise one or more additional components, e.g., sensors, cameras, or input/output devices, such as buttons, displays, touch-screens, etc.

In the embodiment shown in FIG. 1, the remote device 101 comprises a processor 102, memory 104, a wireless network interface 106, and an NFC antenna 108. The processor 102 is electrically coupled to memory 104, which comprises processor executable instructions configured to cause the processor to perform operations described herein. The memory 104 can comprise any suitable tangible (and non-transitory) computer-readable medium such as RAM, ROM, EEPROM, or the like, and embodies program components that configure operation of the remote device 101.

Processor 102 is further coupled to a wireless network interface 106 configured to transmit and receive data. The wireless network interface 106 may represent one or more of any components that facilitate a wireless network connection other than NFC, including an antenna. Examples include, but are not limited to, wireless interfaces such as IEEE 802.11, Bluetooth, Bluetooth Low Energy (BLE), or radio interfaces for accessing cellular telephone networks (e.g., transceiver/antenna for accessing a CDMA, GSM, UMTS, or other mobile communications network).

Processor 102 is further coupled to an NFC antenna 108. NFC antenna 108 comprises one or more components configured to transmit/receive signals. In one embodiment, NFC antenna 108 comprises an interface configured to transmit and receive NFC signals. For example, NFC antenna 108 may comprise an NFC controller IC configured to receive/generate NFC signals, which are transmitted with an appropriately sized antenna based on the dimensions of the remote device and the desired communications range. Further, in some embodiments, NFC antenna 108 and wireless network interface 106 may be integrated into a single component.

As shown in FIG. 1, the local device 150 comprises a wearable sensor apparatus, e.g., a wearable biometric sensor. Examples of such wearable sensors may comprise sensors embedded in wearable devices (e.g., watches, armbands, headbands, hats, shirts, etc.) or purpose built sensors, e.g., a wearable Continuous Glucose Monitors (CGM) or other sensors for monitoring biometric information such as blood pressure, heart rate, oxygen saturation (SpO2 or SvO2), blood sugar, etc. The local device 150 comprises a processor 152, memory 154, wireless network interface 156, NFC antenna 158, and a sensor 160. The processor 152 is electrically coupled to memory 154, which comprises processor executable instructions configured to cause the processor to perform operations described herein. Further, the memory 154 may act as a local data store to store sensor data received from sensor 160. The memory 154 can comprise any suitable tangible (and non-transitory) computer-readable medium such as RAM, ROM, EEPROM, or the like, and embodies program components that configure operation of the local device 150.

Processor 152 of the local device 150 is further coupled to a wireless network interface 106 configured to transmit and receive data. The wireless network interface 156 may represent one or more of any components that facilitate a wireless network connection, other than NFC, including an antenna. Examples include, but are not limited to, wireless interfaces such as IEEE 802.11, Bluetooth, Bluetooth Low Energy (BLE), or radio interfaces for accessing cellular telephone networks (e.g., transceiver/antenna for accessing a CDMA, GSM, UMTS, or other mobile communications network).

Processor 152 of the wearable device is further in communication with an NFC antenna 158. NFC antenna 158 comprises one or more components configured to transmit/receive signals. In one embodiment, NFC antenna 158 comprises an interface configured to transmit and receive NFC signals. For example, NFC antenna 158 may comprise an NFC controller IC configured to receive/generate NFC signals, which are transmitted with an appropriately sized antenna. Further, in some embodiments, NFC antenna 158 and wireless network interface 156 may be integrated into a single component.

Processor 152 is further in communication with a sensor 160, which is configured to monitor one or more features associated with the person that is monitored by sensor 160 of the local device 150. For example, sensor 160 may comprise one or more of e.g., a sensor to monitor brain activity, an Electrocardiogram (EKG), Electroencephalograph (EEG), Magnetoencephalograph (MEG), heart-rate monitor, blood pressure sensor, blood sugar sensor, such as a CGM, an electrochemical sensor, or an analyte sensor, etc.

In operation, once the local device 150 is placed in position, e.g., mounted to the user, the user or a medical professional may activate the local device using an NFC enabled remote device 101, e.g., an NFC enabled smartphone. The user may place the remote device 101 close to the local device 150 and activate NFC transmission on the remote device 101. This NFC transmission is received by the NFC antenna 158 in the local device 150. These NFC signals may be used to generate a current that closes a switch to provide power from a power supply on the local device to the other components on the local device 150 (e.g., to processor 152, memory 154, wireless network interface 156, and/or sensor 160). In such an embodiment, the power supply of the local device 150 may comprise a battery that is specifically designed to provide power to the active components for only a relatively short period of time, such as a few days to a few weeks. This may enable a relatively smaller, lighter, and cheaper battery to be used than would otherwise be required if the battery needed to remain in use, even before the device was applied to the user.

Further, the NFC signals may be used to initiate communication between the local device 150 and the remote device 101. In such an embodiment, the NFC signals may contain pairing information (e.g., one or more of: Bluetooth key information, a network address, login information, authentication information, or a passcode), which the processor 152 uses to activate wireless network interface 156 of local device 150 and pair it with wireless network interface 106 of remote device 101. Once paired the local device may transmit data stored in memory 154 (e.g., data received from sensor 160) or transmit data that is currently being monitored by sensor 160 in substantially real-time. Thus, a user of remote device 101 may be able to review sensor data on a display of remote device 101 or provide that sensor data to a medical professional for review.

Turning now to FIG. 2, FIG. 2 shows an illustrative system 200 for a sensor with multimode wireless communication. As shown in FIG. 2, the system 200 comprises a wearable device 202 (similar to local device 150 described above) and remote device 204 (similar to remote device 101 described above). As is shown in FIG. 2, the wearable device 202 is wearable on the surface of the user's skin. In other embodiments, the wearable device 202 may comprise a device that is surgically implanted or embedded within human tissue.

As shown in FIG. 2, the remote device 204 is in communication with wearable device 202 via Near Field Communication (NFC) signals. Data encoded in the NFC signals may enable remote device 204 to transmit information or control signals to wearable device 202. For example, in one embodiment, remote device 204 may send a control signal to the wearable device 202 to cause the wearable device to transmit data to, or receive data from, remote device 204 via Bluetooth or BLE.

Illustrative Methods for a Sensor with Multimode Wireless Communication

Figure 3:
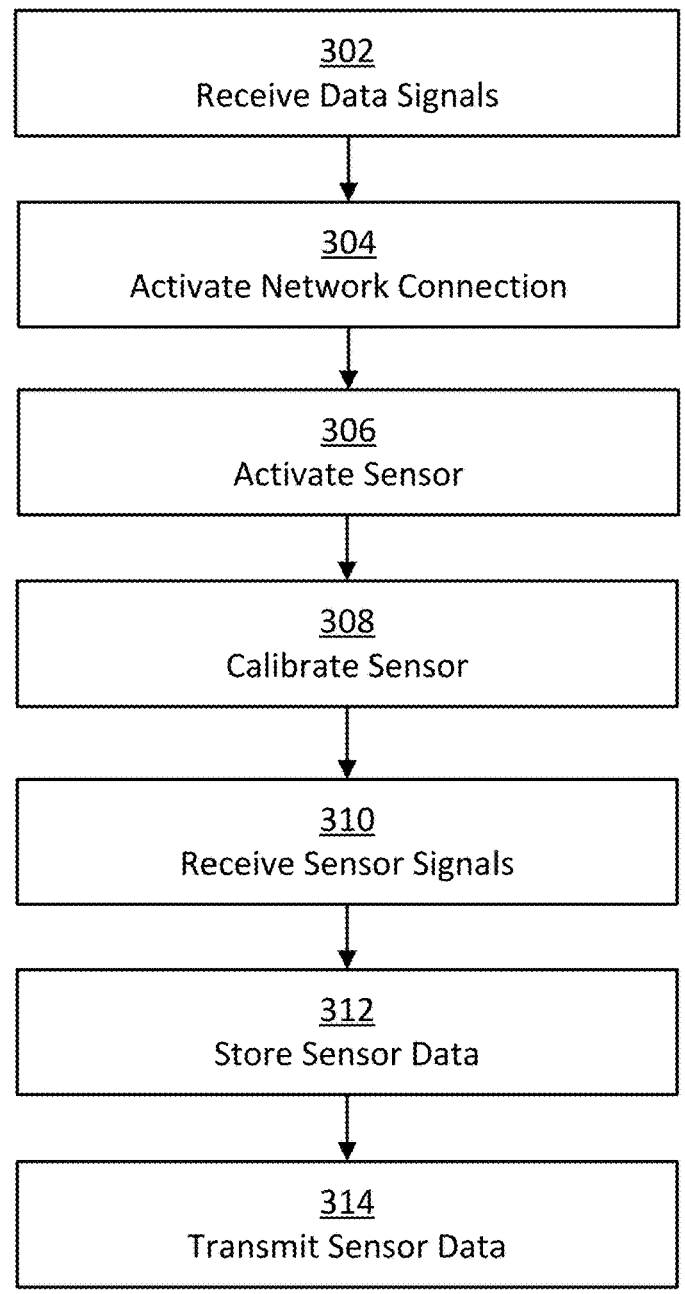
FIG. 3 shows a flow chart for an illustrative method for a sensor with multimode wireless communication according to one embodiment.

FIG. 3 shows a flow chart for an illustrative method for a sensor with multimode wireless communication according to one embodiment. In some embodiments, the steps in FIG. 3 may be performed in a different order. Alternatively, in some embodiments, one or more of the steps shown in FIG. 3 may be skipped, or additional steps not shown in FIG. 3 may be performed. The steps below are described with reference to components described above with regard to system 100 shown in FIG. 1, though examples according to this disclosure may be performed using any suitable device or system according to this disclosure.

The method 300 begins at step 302 when processor 152 receives data signals from remote device 101. The processor may receive data signals transmitted from an NFC antenna 108 of the remote device 101 to the NFC antenna 158 of the local device. In some embodiments, the NFC signals may contain pairing data associated with a wireless network interface 156 of the local device 150. The pairing data may comprise one or more of Bluetooth key information, a network address, login information, authentication information, or a passcode. In other embodiments the NFC signal may contain other or additional information, e.g., calibration information or control information to activate one or more other components of the local device 150.

Next at step 304 the processor 152 activates a wireless network interface 156. As described above, the wireless network interface 156 may comprise one or more of Bluetooth, Bluetooth Low Energy (BLE), or Wi-Fi. Further, the processor 152 may pair the wireless network interface 156 with the wireless network interface 106 of the remote device 101. In some embodiments, the processor 152 may pair the network connections using data received via the NFC signal. For example, the remote device 101 may transmit information such as Bluetooth key information, a network address, login information, authentication information, or a passcode to the local device 150 via NFC signals. The processor 152 may use this information to activate or authenticate a network connection to the remote device 101 via wireless network interface 156.

Then at step 306, the processor 152 activates a sensor 160. The sensor 160 may comprise one or more of a sensor to monitor brain activity, an Electrocardiogram (EKG), Electroencephalograph (EEG), Magnetoencephalograph (MEG), heart-rate monitor, blood pressure sensor, electrochemical sensor, electrochemical sensor, analyte sensor, etc., or some other sensor known in the art. In some embodiments, the sensor 160 may be inactive until receipt of NFC signals or receipt of one or more commands communicated via the NFC signals or via the wireless networks connection established at block 304, which may help to preserve battery life on the local device 150.

Next, at step 308, the processor 152 calibrates the sensor 308. The processor 152 may receive calibration information from the wireless network interface 156, e.g., calibration information received once a connection is established to the remote device 101. Further, in some embodiments, the processor 152 may receive other information such as firmware or software upgrades via the wireless network interface 156 or via NFC antenna 158. The processor 152 may use this information to update the functions on the local device 150.

Then at step 310, the processor 152 receives sensor signals from the sensor 160. In some embodiments the processor 152 may operate sensor 160 substantially continuously or may periodically sample sensor signals provided by the sensor. In other embodiments, the processor 152 may sample sensor data only after a predetermined period of time, or in response to a user input, such as a button press or other command to take a sensor reading. In some embodiments, processor 152 may control the sensor 160 based on data received from the remote device 101 via wireless network interface 156 or via NFC antenna 158, such as by receiving a command from the remote device 101 to provide one or more sensor signals. In some embodiments, this may preserve the life of a power supply of the local device 150.

Next at step 312 the processor 152 stores the sensor data in a memory 154. In some embodiments the processor 152 may store sensor data in memory 154 for later transmission. In some embodiments, processor 152 may store data based on control signals received from wireless network interface 156 or via NFC antenna 158.

Then at step 314, the processor 152 transmits the sensor data to the remote device 101. In some embodiments, the processor 152 may transmit sensor data stored in memory 154 via wireless network interface 156. Alternatively or additionally, in some embodiments, the processor 152 may transmit sensor data in substantially real-time as it is measured by sensor 160. In some embodiments, the transmission of sensor data may occur based on control signals received from wireless network interface 156 or via NFC antenna 158.

Figure 5A:
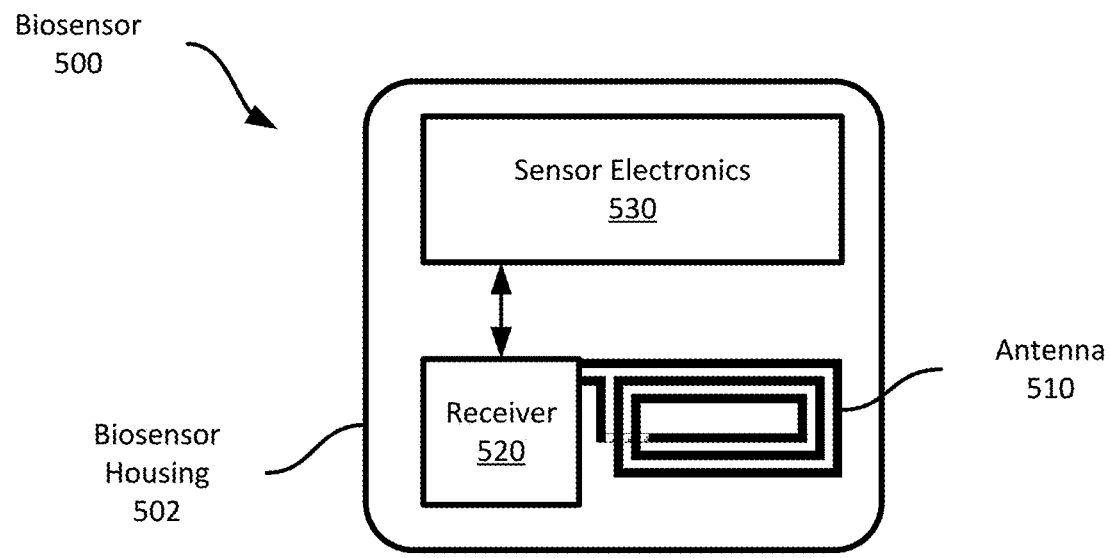
FIGS. 5A-5B show an example wearable biosensor.
Figure 5B:
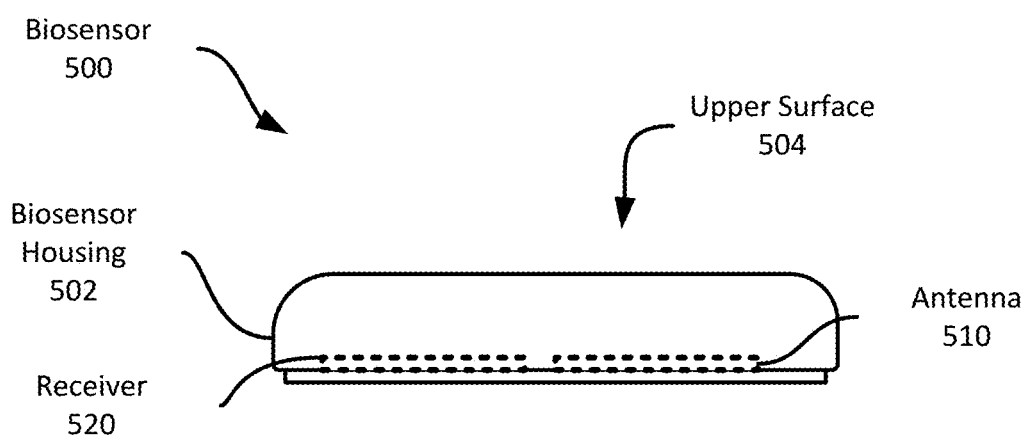

Referring now to FIGS. 5A-5B, FIG. 5A shows a top-down view of an example biosensor 500 usable with one or more systems or methods for enabling NFC communications with a wearable biosensor. The biosensor 500 includes a housing 502 inside which are sensor electronics 530, a wireless receiver 520, and a coil antenna 510. In this example, the biosensor 500 includes sensor electronics 530 that include a CGM, which includes a sensor wire to be inserted into a wearer's skin to measure glucose levels within the wearer's interstitial fluid. However, the sensor electronics 530 may include any suitable biosensor(s). For example, one or more sensors may be incorporated into the biosensor 500, including invasive or non-invasive sensors, such as analyte sensors (e.g., glucose, lactate, alcohol, etc.), blood pressure sensors, pulse sensors, blood oxygen sensors (e.g., SvO2, SpO2, etc.), galvanic skin response sensors, ultraviolet light sensors, etc.

The sensor electronics 530 may include one or more processors, memory, a battery or other power supply (e.g., photovoltaic cells), etc. The sensor electronics 530 are communicatively coupled with the wireless receiver 520 to allow communications between the wireless receiver 520 and the sensor electronics 530. Communications may include data, commands, electrical power, etc. according to different examples.

In this example, the wireless receiver 520 is part of a wireless transceiver that enables wireless communications with a remote device using the coil antenna 510; however it should be appreciated that according to different examples, the biosensor 500 may not include a wireless transceiver, but only a wireless receiver 520. The wireless receiver 520 is configured to receive NFC communications; however, any suitable short-range wireless communications protocol may be employed according to different examples. In the context of this application, "short-range" refers to implementations of communications techniques that have an effective range of a few centimeters ("cm") (e.g., less than 30 cm) without intervening physical obstructions.

The coil antenna 510 is an electrical conductor, e.g., a wire or electrical trace formed on a substrate, formed in a coil shape to enable electromagnetic coupling with another coil antenna via a varying EMF and to electromagnetically couple to the receiver 520. In this example, the coil antenna 510 substantially planar, however, example coil antennas 510 may instead be helical. In this example, the coil antenna 510 has a rectangular shape, suitable coil antennas may have any shape, including circular, ovoid, etc. Further, suitable coil antennas may be substantially planar or may extend along an axis, such as in a helical configuration.

FIG. 5B shows a side view of the biosensor 500, which illustrates the biosensor's components within the biosensor's housing 502. In this view, the receiver 520 and antenna 510 are both positioned on a common substrate on a bottom portion of the biosensor housing. The sensor electronics 530 are also physically coupled to the bottom portion of the biosensor housing 502, however, they are occluded by the receiver 520 and antenna 510 in this view. The bottom portion of the housing 502 refers to the portion of the housing 502 that will be positioned on or adjacent to the wearer's skin or clothing. It should be appreciated that the coil antenna 510 may be positioned at any suitable position within or on the biosensor housing 502. For example, the antenna 510 may be physically coupled to the top portion of the biosensor housing 502 or on an outer surface of the biosensor housing 502, e.g., the top portion of the biosensor housing 502. In such an arrangement, the coil antenna 510 may be communicatively coupled to the receiver 520 by one or more conductors, such as wires or conductive traces, e.g., conductive traces formed on the housing 502.

Referring now to FIGS. 6A-6C, FIGS. 6A-6C illustrate an example biosensor applicator 600 usable with systems and methods for enabling NFC communications with a wearable biosensor. In this example, the biosensor applicator 600 has a housing 602 and two antennas 610, 620, and is configured to accept a biosensor within the housing 602 as will be discussed in more detail with respect to FIGS. 7A-7B below.

In this example, FIG. 6A shows a top-down view of the biosensor applicator 600. In this view, a first antenna 610 of the two antennas is shown as positioned on the inner surface of an upper portion of the housing 602. Upper portion refers to the portion of the housing 602 opposite the portion of the housing 602 into which a biosensor may be inserted. While, in this example, the first antenna 610 is positioned on an inner surface of the housing 602, in some examples, the first antenna 610 may be positioned on an outer surface of the housing 602. Such a configuration may allow the wearer to more easily identify the location of the antenna 610. In this example, the antenna 610 has a substantially planar configuration, though in some examples, it may have a helical configuration.

Referring to FIG. 6B, FIG. 6B shows a top-down cross-sectional view of the interior of the biosensor applicator 600. In this view, a second antenna 620 is positioned within the interior of the housing 602 and is substantially axially aligned with the first coil antenna. As can be seen, each antenna 610, 620 is a coil around an axis running perpendicularly to the respective coil's plane. In this example, the two coils 610, 620 are positioned such that they substantially share a common central axis 612, denoted by an 'x' in FIGS. 6A-6B, and by axis 612 in FIG. 6C. Such an alignment may enable the coils to electromagnetically couple upon application of a varying EMF to one (or both) of the coils. Similar to the first antenna 610, the second antenna 620 in this example has a substantially planar configuration, though in some examples it may have a helical configuration.

It should be appreciated that while the antennas 610, 620 in this example do not have circular cross-section, in some examples, one or both of the antennas 610, 620 may have a substantially circular cross-section. In some examples, however, any suitable coil shape may be employed.

Referring now to FIG. 6C, FIG. 6C shows a side cross-section of the biosensor applicator 600. In this example, the applicator 600 does not include a conductor physically coupling the first coil antenna 610 to the second coil antenna 610; however, other examples do have such a conductor, as will be discussed in more detail below. Thus, in this example the two coil antennas 610, 620 are spaced apart by a distance of a few centimeters. In one example, however, the two coils are spaced apart by a distance of no more than twice a radius of the first or second coil. In some examples, one or both coils may not have a circular shape. In such examples, "radius" refers to a distance from the center axis 612 to an outer edge of the antenna 610, 620.

In this example, the applicator's two coil antennas 610, 620 each have a radius of substantially 4 cm; however, any suitable radius or width may be employed. It should be appreciated, however, that an effective electromagnetic coupling distance may be up to substantially twice the radius or width of an electromagnetic coil in some examples. Therefore, a size of one or more coil antennas may be selected based on a needed effective range. For example, if distance between the biosensor coil antenna 610 and the top surface of the applicator is 6 cm, a single coil antenna, e.g., first antenna 610, may have a radius of substantially 3 cm. Alternatively, if two coil antennas are employed, smaller radii may be employed based on the positions of the coil antennas within the applicator 600.

In operation, a reader device with an NFC transmitter and coil antenna, such as the smartphone 410 shown in FIG. 4 (or the remote devices 101, 204 shown in FIGS. 1 and 2), may be brought within an effective transmission range of the biosensor applicator 600. When the reader device's NFC transmitter is activated, it generates an alternating EMF using its coil antenna, which electromagnetically couples with the first coil antenna 610. The first coil antenna 610 may then electromagnetically couple with the second coil antenna 620, effectively extending the range of the reader device's own coil antenna. Absent the first or second coil antennas 610, 620, the alternating EMF may not be able to effectively penetrate the applicator housing 602 to reach a biosensor within the applicator 600.

Referring now to FIGS. 7A-7B, FIG. 7A shows a side view of an example system 700 for enabling NFC communications with a wearable biosensor. The system 700 includes the biosensor applicator 600 shown in FIGS. 6A-6C, and the biosensor 500 shown in FIGS. 5A-5B. As can be seen, the biosensor 500 is positioned within the applicator 600, forming a monolithic system 700. The monolithic system 700 can be used to apply the biosensor 500 to a wearer's skin. For example, if the biosensor 500 is a CGM, the applicator 600 may include a needle to puncture the wearer's skin and to allow one or more CGM sensor wires to be inserted through the puncture.

As can be seen, the biosensor 500 is positioned within the applicator 600 such that the applicator's two antennas 610, 620 sit above the biosensor 500. And while the biosensor 500 is entirely disposed within the applicator in this example, in other examples, the biosensor 500 may partially protrude from the applicator 600, or it may physically couple to an outer surface of the applicator's housing 602.

In this example, the biosensor's antenna 510 is offset from the coaxially aligned antennas 610, 620 in the applicator; however, in some examples, the biosensor's antenna 510 may be coaxially aligned with the applicator's antennas 610, 620. In addition, in this example, the biosensor's antenna 510 has a smaller radius than the radii of the applicator's antennas 610, 620; however, in some examples, the biosensor's antenna 510 may have substantially the same radius or a larger radius than the applicator's antenna's 610, 620.

In this example, the first antenna 610 is positioned on an inside of the top surface of the applicator 600. Thus, when a reader device, such as a smartphone, energizes its transmission coil antenna within effective range of the first antenna 610, the first antenna 610 electromagnetically couples with the reader device's coil antenna and receives EMF energy from the reader device. The first antenna 610 then uses the received energy received to electromagnetically couple with the second antenna 620. The second antenna 620 then receives the EMF energy from the first antenna 610, and uses the received EMF energy to electromagnetically couple with the biosensor's coil antenna 510, which transfers EMF energy to the biosensor's coil antenna 510. Thus, the arrangement of antennas 510, 610, 620 in the applicator and biosensor effectively extend the range of the reader device's own transmission coil antenna, allowing the energy emitted by the reader device to effectively reach the biosensor's coil antenna 510 despite potentially being outside of an effective range of the transmission coil.

In this example, because the first antenna 610 is located on the interior of the applicator's housing, such as to protect to the first antenna 610 from damage, an alignment marking 630 is provided on the outer top surface of the applicator 600. FIG. 7B shows an example alignment marking 630 to enable a user to more easily align the reader device with the first antenna. In some examples, however, the first antenna 610 may be positioned on the outer top surface of the applicator 600, or may be embedded in the top surface and made visible, e.g., via a transparent window, and such an alignment marking 630 may not be used.

Referring now to FIGS. 8A-8C, FIGS. 8A-8C show an example system 800 for enabling NFC communications with a wearable biosensor. FIG. 8A illustrates a top-down view of a biosensor applicator 802. In this view, a first antenna 810 of the applicator's two antennas 810, 820 is shown as being positioned on the inner surface of an upper portion of the applicator 802, while a second coil antenna 820 is positioned within the interior of the applicator 802. In this example, the applicator's two antennas 810, 820 are coaxially aligned with each other, substantially as described above with respect to FIGS. 6A-6C.

In this example, unlike the example discussed above with respect to FIGS. 6A-6C, the applicator's two antennas are physically and electrically coupled by an electrical conductor 830, such as a wire or an electrical trace formed on the applicator's housing. The electrical conductor 830 enables energy received by the first antenna 810 to be transferred to the second antenna 820. Thus, rather than only employing electromagnetic coupling, the first and second antennas 810, 820 exchange energy via the electrical conductor. Thus, if a reader device is positioned within an effective range of the first antenna 810, the reader device's coil antenna will electromagnetically couple with the first antenna 810. The received energy will then traverse the electrical conductor 830 to the second antenna 820. It should be appreciated that the first antenna 810 will wirelessly electromagnetically couple with the second antenna 820 as well; however, the electrical conductor 830 provides a direct wired conductive pathway to transfer the energy as well. The second antenna 820 will then electromagnetically couple with the biosensor's coil antenna 210. The biosensor's coil antenna 210 may then receive any commands, data, or power transmitted by the reader device.

Thus, similar to the example shown in FIGS. 7A-7B, the applicator's two antennas 810, 820 effectively extend the range of the reader device's coil antenna. Further, the electrical conductor 830 may provide a more efficient pathway for energy transfer between the first and second coil antennas 810, 820 than a wireless electromagnetic coupling. It should be appreciated that while the coil antennas 810, 820 in this example has a substantially planar configuration, in some examples one or both may have a helical configuration.

Figure 9A:
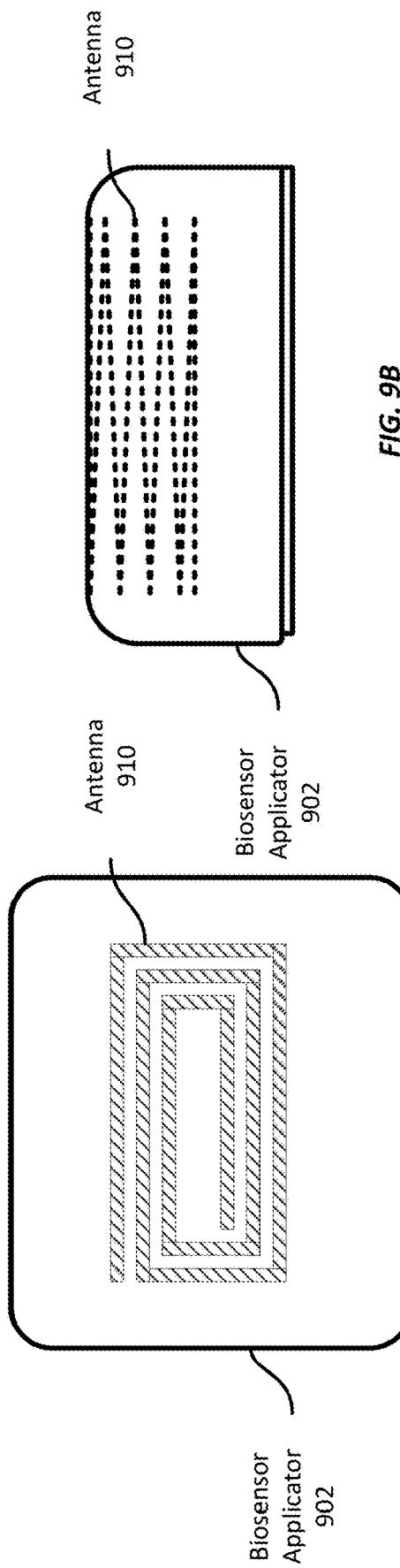
FIGS. 9A-9C show an example wearable biosensor applicator and an example system for enabling NFC communications with a wearable biosensor.
Figure 9B:
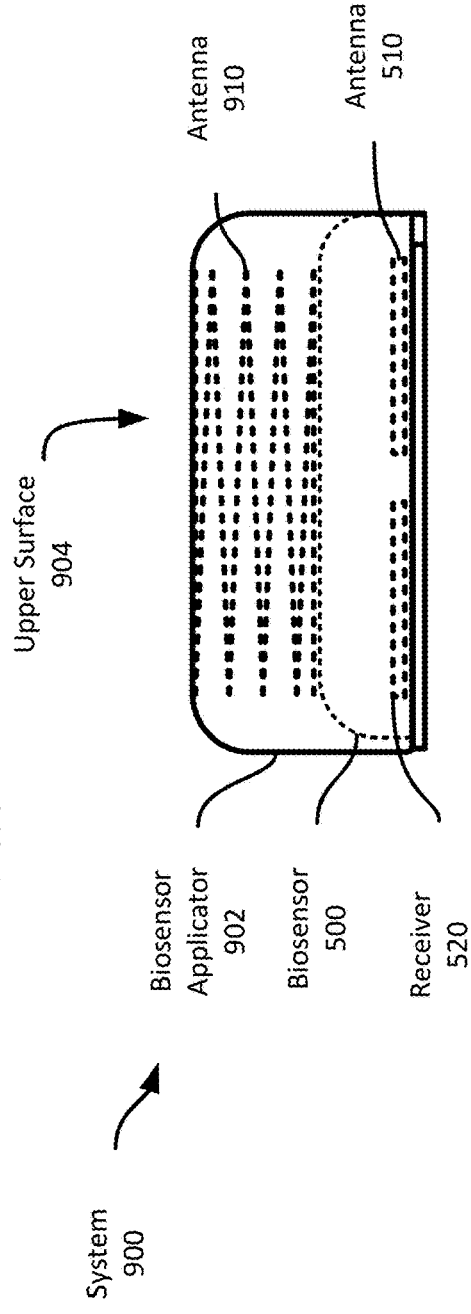
Figure 9C:
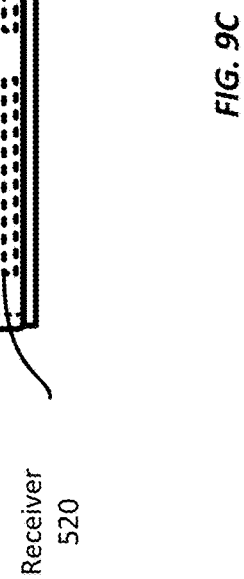

Referring now to FIGS. 9A-9C, FIGS. 9A-9C show an example system 900 for enabling NFC communications with a wearable biosensor. FIG. 9A shows a top-down view of a biosensor applicator 902 having a coil antenna 910. In this example, the biosensor applicator 902 only has one coil antenna within its housing to electromagnetically couple with a reader device and with a biosensor's antenna 510. As can be seen in FIG. 9B, the coil antenna 910 has a helical configuration rather than being substantially planar. Thus, the coil antenna 910 is physically coupled to an inner surface of an upper portion of the applicator's housing and extends towards a bottom surface of the applicator housing along an axis. While the coil antenna 910 in this example is shown with a particular configuration having approximately five turns and a turn pitch (the axial spacing between adjacent turns) of approximately the width of the antenna's conductor, other antenna configurations may have any suitable number of turns or turn pitch.

FIG. 9C shows the system 900, including the biosensor applicator 902 with an installed biosensor 500. As can be seen in this view of the biosensor applicator 902, its coil antenna 910 extends axially towards the biosensor 500. In this example, the applicator's coil antenna 910 extends to within a few millimeters ("mm") from an upper outer surface of the biosensor 500. Such a spacing may provide a more effective electromagnetic coupling between the applicator's coil antenna 910 and the biosensor's coil antenna 510 when the applicator's coil antenna 910 is energized.

In this example, similar to the example shown in FIGS. 6A-6C, the biosensor's coil antenna 510 is not axially aligned with the applicator's antenna 910; however, such an axial alignment may not be necessary in some examples. For example, the energy emitted by the applicator's antenna 910 may be sufficient to enable electromagnetic coupling with a misaligned antenna 510. In some examples, however, the applicator's coil antenna 910 and the biosensor's coil antenna 510 may be designed to be axially aligned with the other.

Figure 10A:
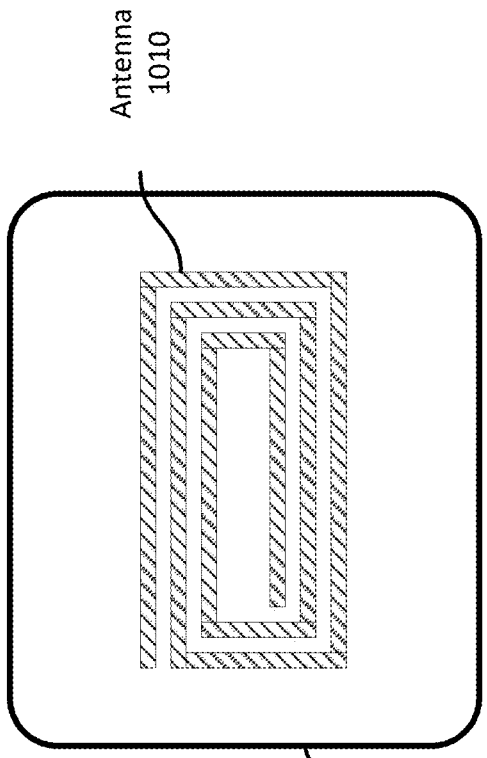
FIGS. 10A-10B show an example wearable biosensor applicator and an example system for enabling NFC communications with a wearable biosensor.
Figure 10B:
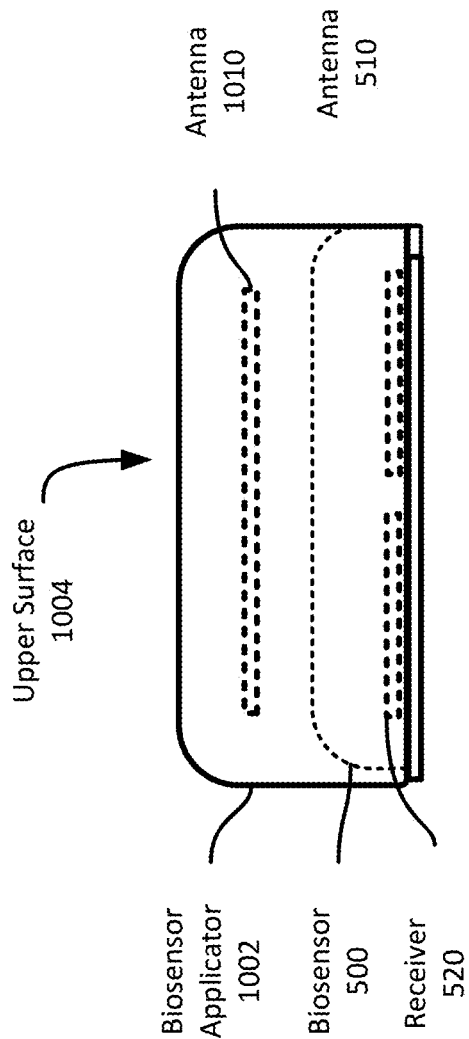

Referring now to FIGS. 10A-10B, these figures show an example system 1000 including a biosensor applicator 1002 and a biosensor 500. In this example, the biosensor applicator 1002 includes only one coil antenna 1010, which is positioned within an interior portion of the biosensor applicator 1002 at a location between the applicator's upper surface 1004 and the biosensor's upper surface 504. Specifically, in this example, the applicator's coil antenna 1010 is positioned equidistant between the applicator's upper surface 1004 and the biosensor's upper surface 504. However, in some examples other positions may be employed. For example, the applicator's coil antenna 1010 may be positioned equidistant between the applicator's upper surface 1004 and the biosensor's coil antenna.

Example applicators or similar devices according to this disclosure employing only one coil antenna, similar to those employing two or more coil antennas as discussed above with respect to FIGS. 6A-8C, may effectively increase the effective range of an NFC or similar coil antenna in a reader device by providing an intermediate electromagnetic coupling between the reader device and a target device, such as a biosensor. In applications where a reader device is obstructed from moving within an effective near-field communications range of a target device, such as due to an intervening device or applicator, example arrangements of one or more intermediate coil antennas, including helical antennas, may be positioned within the intervening device or applicator to enable propagation of such near-field communications from the reader device, through the intervening device, and to the coil antenna of the target device. Such techniques may enable communications through obstacles or over distances that might otherwise impair or prevent NFC communication between a reader device and a target device.

Figure 11:
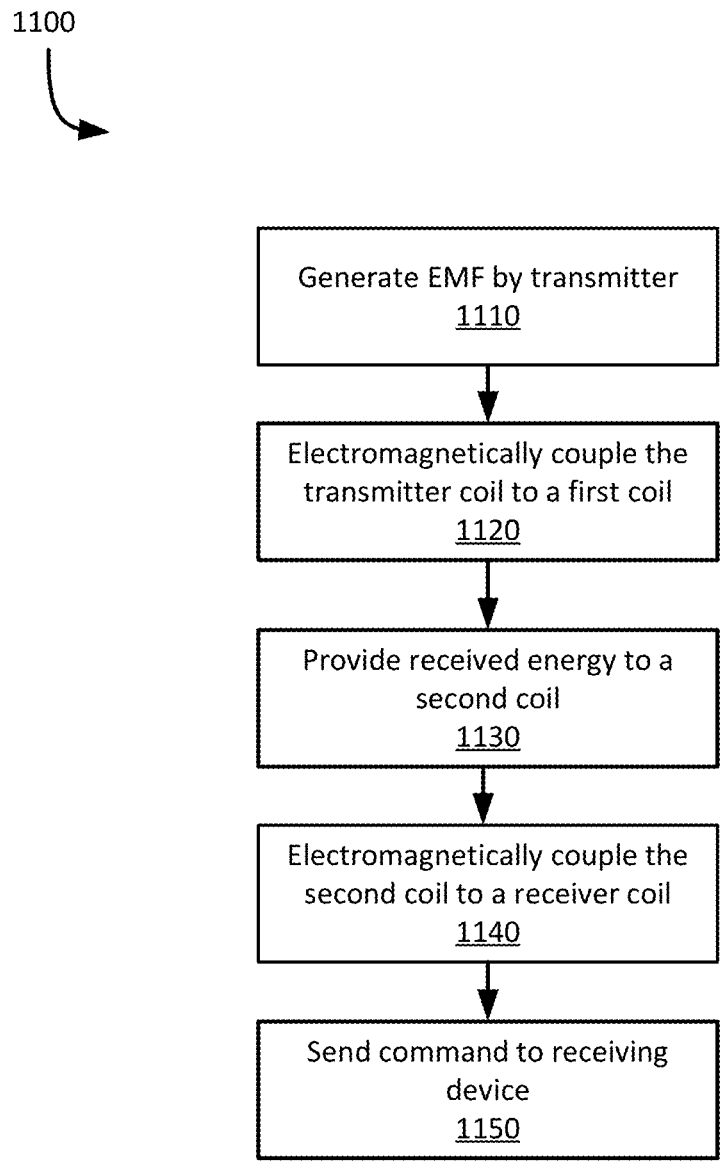
FIGS. 11-12 show example methods for enabling NFC communications with a wearable biosensor.

Referring now to FIG. 11, FIG. 11 shows an example method 1100 for enabling NFC communications with a wearable biosensor. The example method 1100 will be discussed with respect to the example system 600 shown in FIG. 6-7 and the example wireless reader device 1300 shown in FIG. 13, and described in more detail below; however any suitable system and reader device according to this disclosure may be employed, such as the remote devices 101, 204 shown in FIGS. 1 and 2.

At block 1110, a reader device 1300 generates an EMF using a wireless transmitter 1312 that is electrically coupled to a coil antenna 1314. In this example, the reader device 1300 generates a varying EMF using the transmitter 1312 according to a NFC technique; however, any suitable near-field wireless communication technique may be employed.

At block 1120, the reader device 1300 is brought into proximity of a device having a coil antenna. In this example, the device is a system 600 including a biosensor applicator 600 with an installed biosensor 500. The biosensor applicator 600 includes two coil antennas 610, 620. In this example, the reader device is positioned such that the first antenna 610 within the biosensor applicator 600 is within the effective range of the reader device's coil antenna 1314, such as within a few centimeters. After the reader device's coil antenna 1314 is energized by the transmitter 1312 and is generating an EMF, the reader device's coil antenna 1314 electromagnetically couples with the applicator's first antenna 610, thereby transferring energy to the first antenna 610.

At block 1130, the applicator's first coil antenna 610 uses the received energy from the reader device 1300 to electromagnetically couple with the applicator's second antenna 620, thereby transferring energy to it. It should be appreciated that if the device does not include a second antenna, such as in the examples shown in FIGS. 9A-9C and 10A-10B, block 1130 may be omitted. Further, if the device includes more than two antennas, block 1130 may be repeated for each additional antenna, thereby propagating energy transmitted by the reader device 1300 through the successive coil antennas within the device.

At block 1140, the second coil antenna 620 uses received energy from the first antenna 610 to electromagnetically couple to the biosensor's coil antenna 510. The energy received at the biosensor's coil antenna 510 is then conducted to its wireless receiver 520, where it may be used by the biosensor.

At block 1150, the reader device 1300 transmits a command to the biosensor using the indirect electromagnetic coupling, provided by the applicator's first and second coil antennas 610, 620, to the biosensor's coil antenna 510. In this example, the reader device 1300 transmits an activation command to the biosensor 500. The activation command is configured to cause the biosensor to activate, which may include emerging from a sleep or pre-use mode, activating a power supply within the biosensor 500, activating one or more electronic components within the biosensor, etc. In response to the activation command, the biosensor 500 may also transmit a response to the activation command using the indirect electromagnetic coupling between the biosensor's coil antenna 510 and the reader device's coil antenna 1314. And while this example employed an activation command, it should be appreciated that any suitable command or data may be communicated using the indirect electromagnetic coupling between the reader device's coil antenna 1314 and the biosensor's coil antenna 510.

In some examples, rather than transmitting a command or data, the reader device 1300 may provide power to the biosensor 510, such as to charge a battery within the biosensor 500. In some examples, the reader device 1300 may transmit both power to charge a battery and to provide one or more commands to the biosensor.

Figure 12:
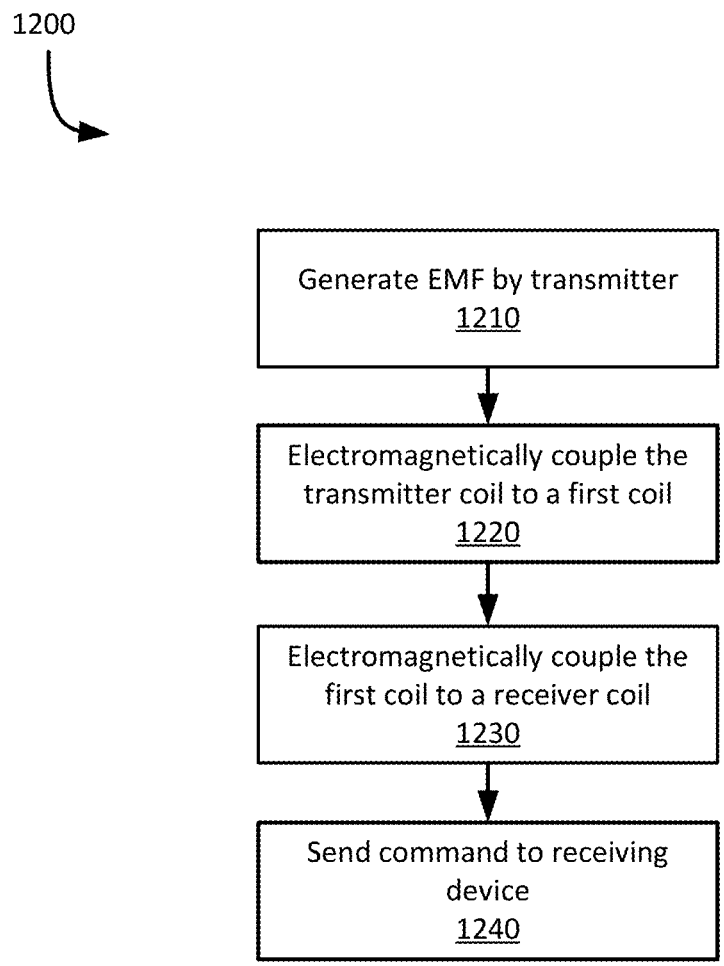

Referring now to FIG. 12, FIG. 12 shows an example method 1200 for enabling NFC communications with a wearable biosensor. The method 1200 will be discussed with respect to the example system 900 shown in FIGS. 9A-9C and the example reader device 1300 shown in FIG. 13, discussed in more detail below; however, any suitable device system or reader device may be employed according to different examples.

At block 1210, the reader device's wireless transmitter 1312 generates an EMF using its coil antenna 1314 substantially as described above with respect to block 1110.

At block 1220, the reader device's coil antenna 1314 electromagnetically couples to the applicator's coil antenna 910, substantially as discussed above with respect to block 1120.

At block 1230, the applicator's coil antenna 910 electromagnetically couples to the applicator's coil antenna 910 substantially as discussed above with respect to block 1140. Thus, in contrast to the example shown in FIG. 11, this example method 1200 uses only one coil within the applicator device 902; however, as discussed above with respect to block 1130 of method 1100, any suitable number of coil antennas may be employed.

At block 1240, the reader device 1300 transmits a command to the biosensor substantially as discussed above with respect to block 1150.

Figure 13:
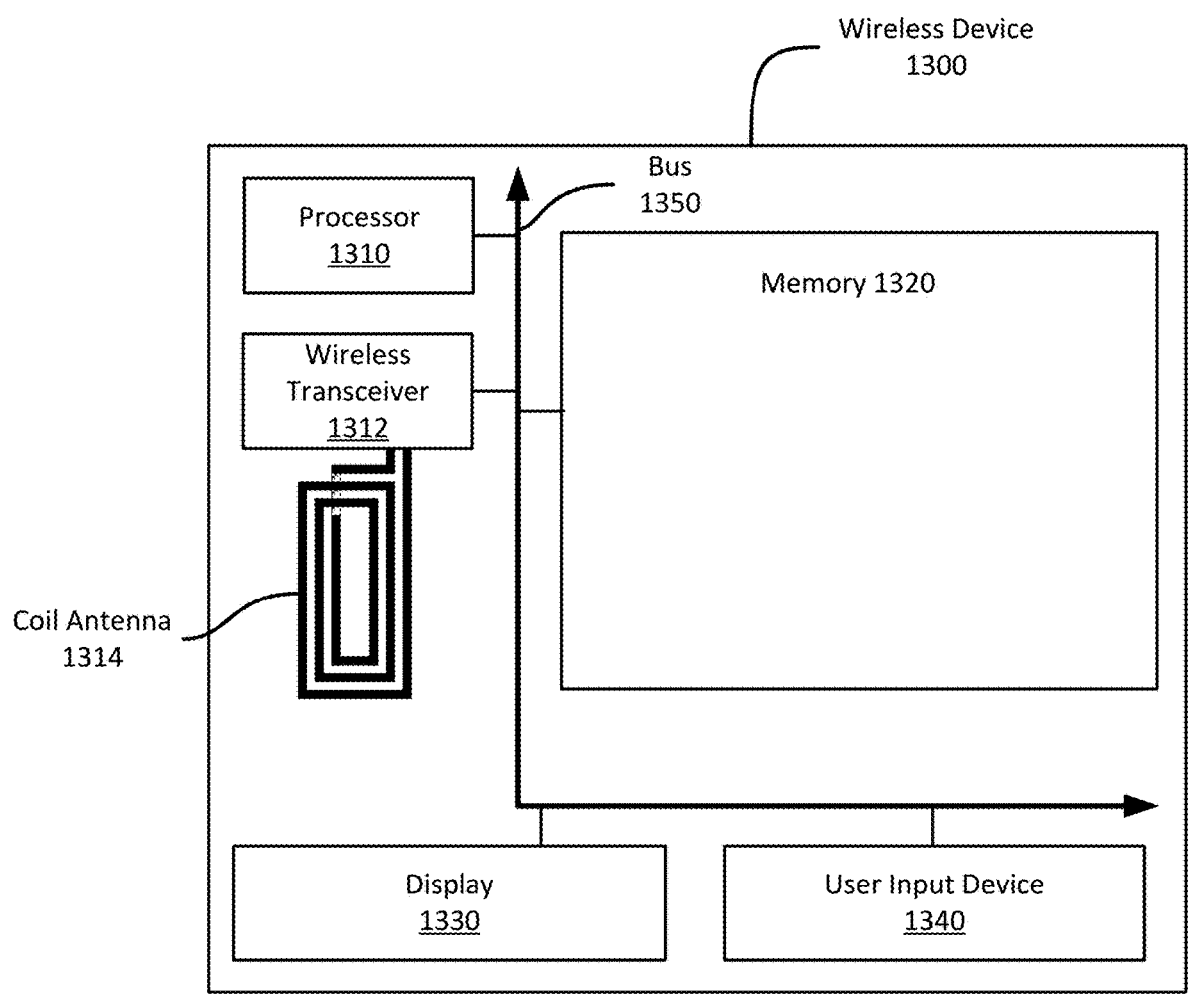
FIG. 13 shows an example wireless computing device.

Referring now to FIG. 13, FIG. 13 shows an example computing device 1300. In the example shown in FIG. 13, the computing device includes a processor 1310, a memory 1320, a wireless transceiver 1312, a display 1330, a user input device 1340, and a bus 1350. In this example, the computing device 1300 comprises a cellular smartphone, but may be any suitable computing device, include a cellular phone, a laptop computer, a tablet, a phablet, a personal digital assistant (PDA), wearable device, etc. The processor 1310 is configured to employ bus 1350 to execute program code stored in memory 1320, to output display signals to a display 1330, and to receive input from the user input module 1340. In addition, the processor 1310 is configured to transmit information to the wireless transceiver 1312. The wireless transceiver 1312 is configured to transmit and receive wireless signals via coil antenna 1314. For example, the wireless transceiver 1312 may be configured to generate an EMF to electromagnetically couple the coil antenna 1314 with another coil antenna, such as may incorporated into any of the devices described above.

Advantages of a Sensor with Multimode Wireless Communication

There are numerous advantages of a sensor with multimode wireless communication. For example, embodiments of the present disclosure preserve the battery life of sensors because power consuming circuitry on the sensor may remain inactive until the device is placed in position and activated. This may preserve battery life by keeping components inactive longer. This may add value to these devices be enabling them to be used for longer periods of time. Battery life may be further enhanced by maintaining only activating a network connection when a receiving/transmitting device is within range.

Further, embodiments of the present disclosure may ease the process for pairing a wearable sensor with a remote device. This may ease the process for transmitting recorded data or providing updates to the local device. Further, embodiments of the present disclosure may simplify the process of coupling a network connection between the remote device and the local device because the user is not required to manually enter network information, which instead may be transmitted via NFC signals.

Further, this may enhance security of the process of authenticating the network because a remote device may not be able to pair with the local device without first receiving NFC data. This enhances security because only devices that are close enough to the local device to receive NFC signals will be able to pair, providing security be proximity. Further, in some embodiments, authentication information may be changed each time a remote device pairs with the local device, thus ensuring that only the intended remote device is able to pair with the local device. These security features may be particularly preferable in biosensor applications in which security, both for privacy and to comply with government regulations such as HIPAA.

In addition, by incorporating one or more intermediate coil antennas into an applicator device to relay EMF energy to a wearable device. EMF energy, e.g., NFC communications or power, may be used to send commands to the wearable device or to power the wearable device (or both). Thus, the applicator enables NFC communications that might otherwise be prevented or degraded because the applicator itself prevents the a remote device 101, 204, 410, 1300 from moving within effective communications range of the wearable device's coil antenna, or otherwise interferes with communication between the two. Further, by extending the range of NFC communications, example systems according to this disclosure can further ease the process of establishing wireless communications with a wearable device while it is installed within an applicator or other device, e.g., to establish a Bluetooth or BLE connection.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. Processors used to implement methods described herein may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

The invention claimed is:

1. A system comprising:
    a biosensor applicator comprising:
        a housing defining a cavity configured to receive and physically couple to a biosensor device, and to apply the biosensor device to a wearer;
        an applicator coil antenna oriented around a first axis; and
    a biosensor device comprising:
        a biosensor coil antenna;
        a first wireless transceiver electrically coupled to the biosensor coil antenna;
        a Bluetooth antenna; and
        a second wireless transceiver coupled to the Bluetooth antenna;
    wherein the biosensor device is physically coupled to the biosensor applicator and positioned at least partially within the cavity; and
    wherein the applicator coil antenna is configured to wirelessly receive electromagnetic ("EM") energy from a remote coil antenna and wirelessly provide at least a first portion of the received EM energy to the biosensor coil antenna.

2. The system of claim 1, wherein the biosensor device further comprises a processor configured to:
    receive, from the first wireless transceiver, data signals from a remote device via the applicator coil antenna, the data signals comprising Bluetooth authentication information;
    compare the Bluetooth authentication information to device information associated with the biosensor device; and
    enable a Bluetooth network connection to the remote device based on the Bluetooth authentication information.

3. The system of claim 2, the biosensor device further comprising a biosensor and a memory configured to store sensor data from the biosensor, and wherein the processor is further configured to:
    determine a level of access of a plurality of levels of access to sensor data stored in the memory based on the data signals; and
    control access by the remote device to the sensor data stored in the memory based on the level of access.

4. The system of claim 3, wherein the plurality of levels of access comprise a user access level, a healthcare provider access level, and a caretaker access level.

5. The system of claim 4, wherein:
    the user access level enables access to real-time sensor data; and
    the health care provider access level enables access to historical sensor data and access to calibrate or recalibrate the biosensor.

6. The system of claim 1, wherein applicator coil antenna is a first applicator coil antenna, and wherein the biosensor applicator further comprises:
    a second applicator coil antenna positioned substantially coaxially with respect to the first applicator coil antenna,
    wherein the second applicator coil antenna is configured to wirelessly receive electromagnetic ("EM") energy from a transmitter coil antenna of a remote device and provide at least a first portion of the received EM energy to the first applicator coil antenna.

7. The system of claim 1, wherein the biosensor device is a continuous glucose monitor.

8. The system of claim 1, wherein the applicator coil antenna is substantially planar.

9. The system of claim 1, wherein the applicator coil antenna is substantially helical.

10. A method comprising:
    wirelessly receiving, by an applicator antenna coil of a biosensor applicator, electromagnetic ("EM") energy from a remote coil antenna of a remote device, the EM energy comprising data signals, the biosensor applicator comprising a housing and the applicator antenna coil, the housing defining a cavity configured to receive and physically couple to a biosensor device, and to apply the biosensor device to a wearer and the applicator antenna coil, and wherein the applicator antenna coil is oriented around a first axis;
    wirelessly providing at least a first portion of the received EM energy to a biosensor coil antenna of a biosensor device, the at least a first portion of the received EM energy comprising the data signals, the data signals comprising Bluetooth authentication information, the biosensor device comprising the biosensor coil antenna, a first wireless transceiver electrically coupled to the biosensor coil antenna, a Bluetooth antenna, and a second wireless transceiver coupled to the Bluetooth antenna, wherein the biosensor device is physically coupled to the biosensor applicator and positioned at least partially within the cavity:
    receiving by a processor of the biosensor device, the data signals from the biosensor coil antenna;
    compare the Bluetooth authentication information to device information associated with the biosensor device; and
    enable a Bluetooth network connection to the remote device based on the Bluetooth authentication information.

11. The method of claim 10, the biosensor device further comprising a biosensor and a memory configured to store sensor data from the biosensor, and wherein the method further comprising:
    determining a level of access of a plurality of levels of access to sensor data stored in the memory based on the data signals; and
    controlling access by the remote device to the sensor data stored in the memory based on the level of access.

12. The method of claim 11, wherein the plurality of levels of access comprise a user access level and a healthcare provider access level.

13. The method of claim 12, wherein:
    the user access level enables access to real-time sensor data; and
    the health care provider access level enables access to historical sensor data and access to calibrate or recalibrate the biosensor.

14. The method of claim 10, wherein the applicator antenna coil is a first applicator antenna coil, and further comprising:
- receiving, by a second applicator antenna coil of the biosensor applicator, EM energy from a transmitter antenna coil of a remote device;
- providing a portion of the received EM energy from the transmitter antenna coil of a remote device to the first applicator coil antenna; and
- wherein the second applicator antenna coil is a part of the biosensor applicator and is positioned substantially coaxially with respect to the first applicator antenna coil.

* * * * *